(12) United States Patent
Sacolick et al.

(10) Patent No.: US 11,846,691 B2
(45) Date of Patent: Dec. 19, 2023

(54) SYSTEMS AND METHODS FOR PERFORMING MAGNETIC RESONANCE IMAGING WITH REDUCED OPERATOR INTERACTION

(71) Applicant: Hyperfine Operations, Inc., Guilford, CT (US)

(72) Inventors: Laura Sacolick, Guilford, CT (US); Rafael O'Halloran, Guilford, CT (US); Hadrien A. Dyvorne, New York, NY (US); Khan Mohammad Siddiqui, Hinsdale, IL (US); Michal Sofka, Princeton, NJ (US); Prantik Kundu, Branford, CT (US); Tianrui Luo, New Haven, CT (US)

(73) Assignee: Hyperfine Operations, Inc., Guilford, CT (US)

( * ) Notice: Subject to any disclaimer, the term of this patent is extended or adjusted under 35 U.S.C. 154(b) by 0 days.

(21) Appl. No.: 17/687,309

(22) Filed: Mar. 4, 2022

(65) Prior Publication Data

US 2022/0283253 A1 Sep. 8, 2022

Related U.S. Application Data

(60) Provisional application No. 63/156,628, filed on Mar. 4, 2021.

(51) Int. Cl.
*G01V 3/00* (2006.01)
*G01R 33/54* (2006.01)
*G01R 33/561* (2006.01)

(52) U.S. Cl.
CPC ........ *G01R 33/543* (2013.01); *G01R 33/5611* (2013.01)

(58) Field of Classification Search
CPC . G01R 33/543; G01R 33/5611; A61B 5/0037; A61B 5/055
(Continued)

(56) References Cited

U.S. PATENT DOCUMENTS 6,980,847 B2 12/2005 Peshkovsky et al.
8,520,920 B2 8/2013 Guehring et al.
(Continued)

FOREIGN PATENT DOCUMENTS

CN 113853526 A 12/2021

OTHER PUBLICATIONS

Invitation to Pay Additional Fees for International Application No. PCT/US2022/018968 dated Jun. 22, 2022.
(Continued)

*Primary Examiner* — Walter L Lindsay, Jr.
*Assistant Examiner* — Frederick Wenderoth
(74) *Attorney, Agent, or Firm* — Foley & Lardner LLP

(57) ABSTRACT

Techniques are provided for imaging a subject. A magnetic resonance imaging (MRI) system may use at least one RF coil to generate an initial MR data set for an initial image of the subject. The MRI system may use the initial MR image to determine a difference in orientation between a current orientation of the subject in the initial MR image and a target orientation of the subject. The MRI system may use the determined difference in orientation to determine an adjustment to a gradient pulse sequence for controlling at least one gradient coil. The MRI system may apply the determined adjustment to the gradient pulse sequence to obtain an adjusted gradient pulse sequence. The MRI system may generate an adjusted MR data set using the adjusted gradient pulse sequence, and a second MR image of the subject using the adjusted MR data set.

19 Claims, 12 Drawing Sheets

(58) Field of Classification Search
USPC .......................................................... 324/309
See application file for complete search history.

(56) References Cited

U.S. PATENT DOCUMENTS

| | | | |
|---|---|---|---|
| 8,565,505 B2 | 10/2013 | Bergmans et al. | |
| 9,295,406 B2 | 3/2016 | Zuehlsdorff et al. | |
| 10,635,930 B2 | 4/2020 | Geiger et al. | |
| 11,176,697 B2 | 11/2021 | Traverso et al. | |
| 2003/0178995 A1* | 9/2003 | Peshkovsky | G01R 33/56509 324/309 |
| 2010/0130849 A1 | 5/2010 | Tao et al. | |
| 2011/0228998 A1 | 9/2011 | Vaidya et al. | |
| 2018/0172784 A1 | 6/2018 | Brunner et al. | |

OTHER PUBLICATIONS

International Search Report and Written Opinion for International Application No. PCT/US2022/018968 dated Aug. 16, 2022.
[No Author Listed], AutoAlign. Siemens Healthineers. 2022. 5 pages. https://www.siemens-healthineers.com/en-us/magnetic-resonance-imaging/options-and-upgrades/clinical-applications/autoalign [Last accessed Jul. 21, 2022].
[No Author Listed], Canon Software. The Ultimate, Intuitive MR Interface. Canon Medical Systems USA. 2022. https://us.medical.canon/products/magnetic-resonance/technology/canon-software/ [Last accessed Jul. 21, 2022].
[No Author Listed], Extending the power of MR. Philips Magnetic Resonance. 2017. 62 pages.
[No Author Listed], READYBrain. GE Healthcare. 2022. 2 pages. https://www.gehealthcare.com/products/magnetic-resonance-imaging/mr-applications/readybrain [Last accessed Jul. 21, 2022].
[No Author Listed], SmartExam Brain. Philips. 2022. 10 pages. https://www.usa.philips.com/healthcare/product/HCNMRB514/smartexam-brain-mr-clinical-application [Last accessed Jul. 21, 2022].
[No Author Listed], Certificate of Need Application. Rutland Medical Center. Oct. 21, 2021. 227 pages.
Hayne, GE Healthcare Announces FDA Clearance of MR Systems Optima MR360 and Brivo MR355 to Address Demand for Productivity, Versatility and Value. GE Press Release. Mar. 2011. 3 pages. https://www.ge.com/news/press-releases/ge-healthcare-announces-fda-clearance-mr-systems-optima-mr360-and-brivo-mr355 [Last accessed Jul. 21, 2022].
Padron, Specialty Scanner. A GE Healthcare MR publication. Autumn 2010:54-5.
Runge, AutoAlign. Clinical-MRI. 2022. 4 pages. http://clinical-mri.com/autoalign/ [Last Accessed Jul. 21, 2022].
Young et al., Automated planning of MRI neuro scans. Proc of SPIE 2006;6144. 8 pages.

* cited by examiner

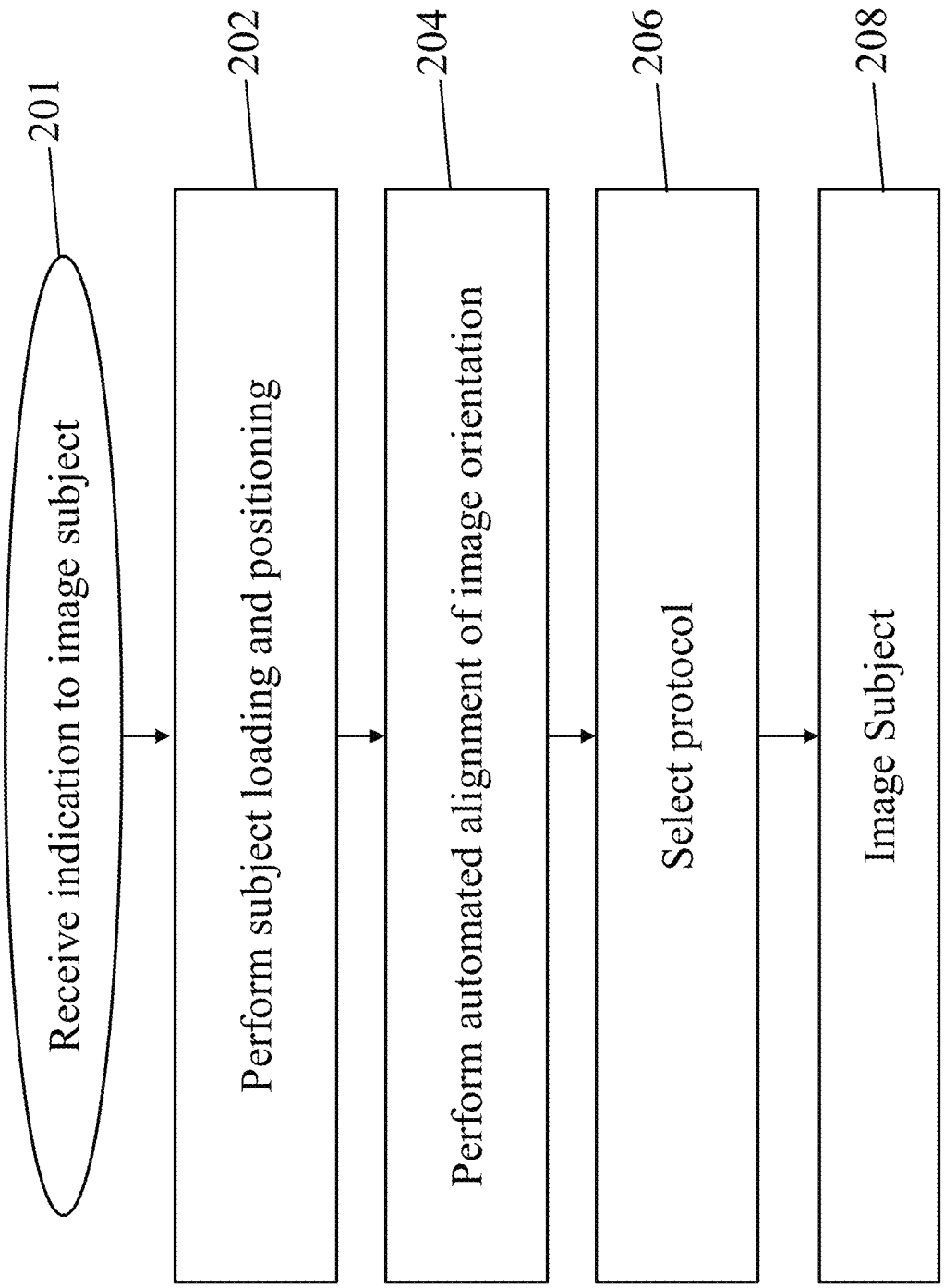

SYSTEMS AND METHODS FOR PERFORMING MAGNETIC RESONANCE IMAGING WITH REDUCED OPERATOR INTERACTION

CROSS-REFERENCE TO RELATED APPLICATIONS

This application claims the benefit under 35 U.S.C. § 119(e) of U.S. provisional patent application Ser. No. 63/156,628, entitled "SYSTEMS AND METHODS FOR PERFORMING MAGNETIC RESONANCE IMAGING WITH REDUCED OPERATOR INTERACTION" filed Mar. 4, 2021, which is incorporated by reference in its entirety herein.

BACKGROUND

Magnetic resonance imaging provides an important imaging modality for numerous applications and is widely utilized in clinical and research settings to produce images of the inside of the human body. MRI is based on detecting magnetic resonance (MR) signals, which are electromagnetic waves emitted by atoms in response to state changes resulting from applied electromagnetic fields. Nuclear magnetic resonance (NMR) techniques involve detecting MR signals emitted from the nuclei of excited atoms upon the re-alignment or relaxation of the nuclear spin of atoms in an object being imaged (e.g., atoms in the tissue of the human body). Detected MR signals may be processed to produce images, which in the context of medical applications, allows for the investigation of internal structures and/or biological processes within the body for diagnostic, therapeutic and/or research purposes.

SUMMARY

Some embodiments provide for a method for imaging a subject using a magnetic resonance (MR) imaging (MRI) system including at least one gradient coil, at least one radio-frequency (RF) coil, and at least one controller, the method comprising: receiving an indication to image the subject using the MRI system; and in response to receiving the indication, with the at least one controller: generating, using the at least one RF coil, an initial MR data set for generating an initial image of the subject; determining, using the initial MR image of the subject, a difference in orientation between a current orientation of the subject in the initial MR image and a target orientation of the subject; determining, using the determined difference in orientation, an adjustment to a gradient pulse sequence for controlling the at least one gradient coil; applying the determined adjustment to the gradient pulse sequence to obtain an adjusted gradient pulse sequence; generating an adjusted MR data set using the adjusted gradient pulse sequence; and generating a second MR image of the subject using the adjusted MR data set.

In some embodiments there is provided a magnetic resonance (MR) imaging (MRI) system for imaging a subject, the MRI system comprising: at least one gradient coil; at least one radio-frequency (RF) coil; and at least one controller configured to: receive, an indication to image the subject using the MRI system; and in response to receiving the indication, with the at least one controller: generate, using the at least one RF coil, an initial MR data set for generating an initial image of the subject; determine, using the initial MR image of the subject, a difference in orientation between a current orientation of the subject in the initial MR image and a target orientation of the subject; determine, using the determined difference in orientation, an adjustment to a gradient pulse sequence for controlling the at least one gradient coil; apply the determined adjustment to the gradient pulse sequence to obtain an adjusted gradient pulse sequence; generate an adjusted MR data set using the adjusted gradient pulse sequence; and generate a second MR image of the subject using the adjusted MR data set.

In some embodiments there is provided at least one tangible computer-readable storage medium having encoded thereon executable instructions that, when executed by at least one computer hardware processor, cause the at least one computer hardware processor to perform a method for imaging a subject using a magnetic resonance (MR) imaging (MRI) system, the MRI system comprising at least one gradient coil, at least one radio-frequency (RF) coil, and at least one controller, the method comprising: receiving an indication to image the subject using the MRI system; in response to receiving the indication, with the at least one controller; generating, using the at least one RF coil, an initial MR data set for generating an initial image of the subject; determining, using the initial MR image of the subject, a difference in orientation between a current orientation of the subject in the initial MR image and a target orientation of the subject; determining, using the determined difference in orientation, an adjustment to a gradient pulse sequence for controlling the at least one gradient coil; applying the determined adjustment to the gradient pulse sequence to obtain an adjusted gradient pulse sequence; generating an adjusted MR data set using the adjusted gradient pulse sequence; and generating a second MR image of the subject using the adjusted MR data set.

BRIEF DESCRIPTION OF THE DRAWINGS

Various aspects and embodiments of the disclosed technology will be described with reference to the following figures. It should be appreciated that the figures are not necessarily drawn to scale. For purposes of clarity, not every component may be labeled in every drawing.

FIG. 2 illustrates an embodiment of a method for performing magnetic resonance imaging with reduced operator interaction, in accordance with some embodiments of the technology described herein.

DETAILED DESCRIPTION

Figure 1:
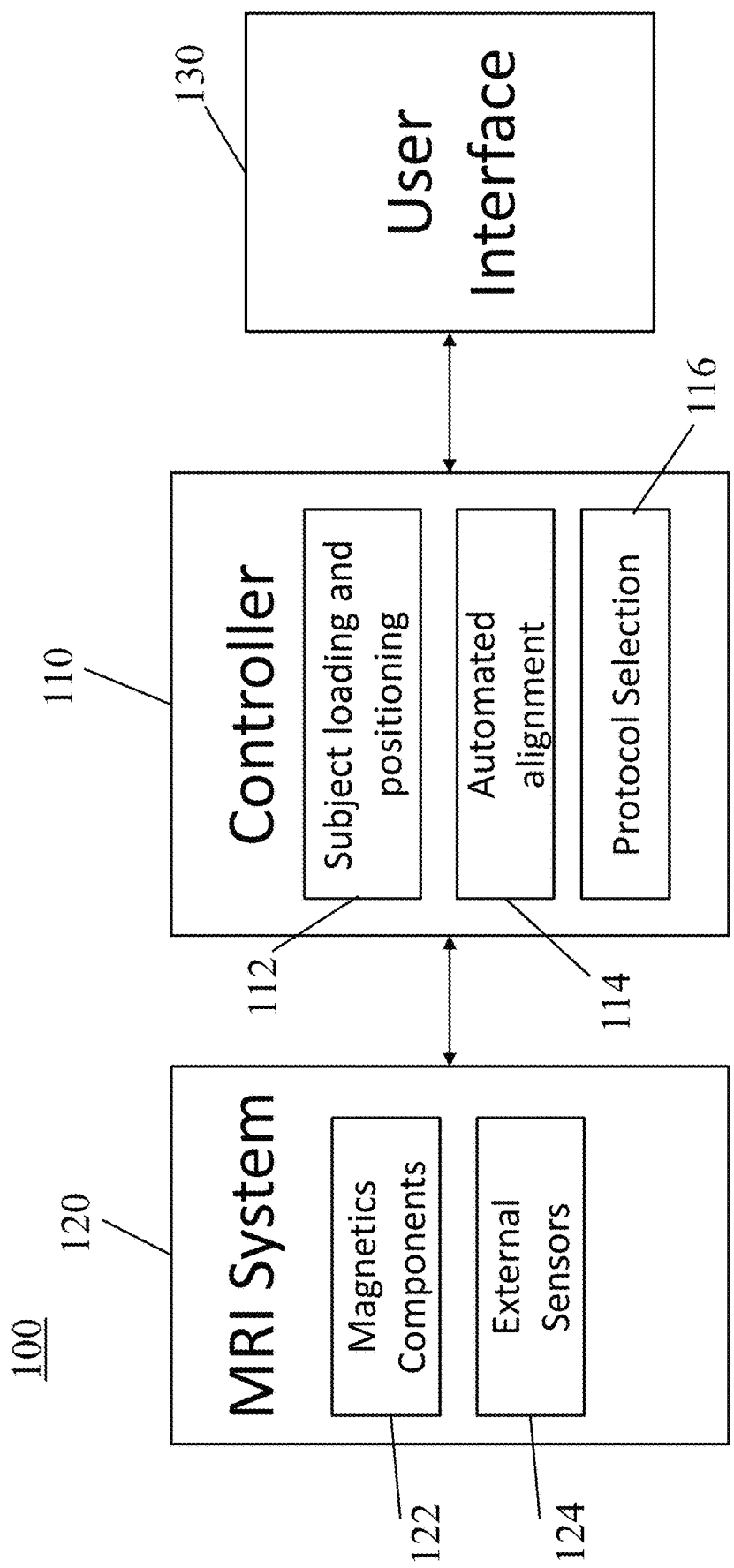
FIG. 1 illustrates a system for performing magnetic resonance imaging with reduced operator interaction, in accordance with some embodiments of the technology described herein.

Aspects of the technology described herein relate to systems and methods for performing magnetic resonance imaging with reduced operator interaction. Conventional MRI systems require a trained technician to perform a number of actions in order to acquire a magnetic resonance image of a subject. In some embodiments, to acquire an MR image of a subject, a user may be required to (1) load the subject (e.g., a human subject, animal subject, or phantom) into an imaging region of the MRI system; (2) plan the image orientation; and (3) select the appropriate protocol (e.g., the appropriate series of pulse sequences) to perform MR imaging. Some or all of these actions may require in-depth training before a user is able to properly carry out these actions. Accordingly, conventional MRI systems may only be able to be operated by trained professionals, thus limiting the availability of MRI where use of MRI would otherwise be beneficial.

Portable low-field MRI systems may be operated by untrained personnel not familiar with how to operate the system to perform MR imaging. One or more possible solutions to this issue are described herein. Thus, an untrained user may be able to operate an MRI system to perform image acquisition. In some embodiments, the MRI system may be configured such that a method for imaging a subject may be performed with reduced operator interaction, and in an embodiment, in response to an indication to begin imaging.

Thus, aspects of the technology described herein relate to systems and methods for performing magnetic resonance imaging with reduced operator interaction. In some embodiments, there may be provided a method for imaging a subject using a magnetic resonance (MR) imaging (MRI) system including at least one gradient coil, at least one radio-frequency (RF) coil, and at least one controller, the method comprising: receiving an indication to image the subject using the MRI system; and in response to receiving the indication, with the at least one controller: generating, using the at least one RF coil, an initial MR data set for generating an initial image of the subject; determining, using the initial MR image of the subject, a difference in orientation between a current orientation of the subject in the initial MR image and a target orientation of the subject; determining, using the determined difference in orientation, an adjustment to a gradient pulse sequence for controlling the at least one gradient coil; applying the determined adjustment to the gradient pulse sequence to obtain an adjusted gradient pulse sequence; generating an adjusted MR data set using the adjusted gradient pulse sequence; and generating a second MR image of the subject using the adjusted MR data set. In some embodiments, the method further comprises generating the initial MR image using the initial MR data set.

In some embodiments, determining the difference in orientation between the current orientation of the subject and the target orientation of the subject comprises comparing the initial MR image of the subject to a template MR image having the target orientation.

In some embodiments, determining the difference in orientation comprises determining the difference in orientation between the current orientation of the subject in the initial MR image and the target orientation of the subject in the template MR image about each of three substantially perpendicular axes.

In some embodiments, determining the difference in orientation between the current orientation of the subject and the target orientation of the subject comprises determining a difference in orientation between a portion of the initial MR image and a portion of the template MR image.

In some embodiments, the method further comprises, based on the initial MR image of the subject and/or information about the at least one RF coil, determining a type of the subject. In some embodiments, determining the type of the subject comprises identifying an anatomy that the subject comprises. In some embodiments, determining the type of the subject comprises identifying the subject as one of a human subject, a non-human animal subject, or a phantom.

In some embodiments, the method further comprises based on the initial MR image and/or an anatomy that the subject comprises, identifying one or more candidate pulse sequences for controlling the at least one RF coil and wherein generating the adjusted MR data set further comprises using the identified one or more candidate pulse sequences.

In some embodiments, determining the difference in orientation further comprises determining the difference in orientation using information about the at least one RF coil.

In some embodiments, the method further comprises determining, using the determined difference in orientation, an adjustment to an RF pulse sequence for controlling the at least one RF coil; applying the determined adjustment to the RF pulse sequence to obtain an adjusted RF pulse sequence; and wherein generating the adjusted MR data set further comprises using the adjusted RF pulse sequence.

In some embodiments, the method further comprises determining, using the determined difference in orientation, an adjustment to image reconstruction parameters to compensate for the adjusted gradient pulse sequence and the adjusted RF pulse sequence; and wherein generating the second MR image of the subject further comprises using the determined adjustment to the image reconstruction parameters.

In some embodiments, the acquiring the initial MR data set, determining the difference in orientation, determining the adjustment to the gradient pulse sequence, generating the adjusted MR data set and generating the second MR with the at least one controller is performed autonomously in response to receiving the indication.

In some embodiments there is provided a magnetic resonance (MR) imaging (MRI) system for imaging a subject, the MRI system comprising: at least one gradient coil; at least one radio-frequency (RF) coil; and at least one controller configured to: receive, an indication to image the subject using the MRI system; and in response to receiving the indication, with the at least one controller: generate, using the at least one RF coil, an initial MR data set for generating an initial image of the subject; determine, using the initial MR image of the subject, a difference in orientation between a current orientation of the subject in the initial MR image and a target orientation of the subject; determine, using the determined difference in orientation, an adjustment to a gradient pulse sequence for controlling the at least one gradient coil; apply the determined adjustment to the gradient pulse sequence to obtain an adjusted gradient pulse sequence; generate an adjusted MR data set using the adjusted gradient pulse sequence; and generate a second MR image of the subject using the adjusted MR data set.

In some embodiments, a strength of a $B_0$ magnetic field generated by the MRI system is greater than or equal to 50 mT and less than or equal to 0.1 T.

In some embodiments there is provided at least one tangible (e.g., non-transitory) computer-readable storage medium having encoded thereon executable instructions that, when executed by at least one computer hardware processor, cause the at least one computer hardware processor to perform a method for imaging a subject using a magnetic resonance (MR) imaging (MRI) system, the MRI system comprising at least one gradient coil, at least one radio-frequency (RF) coil, and at least one controller, the method comprising: receiving an indication to image the subject using the MRI system; in response to receiving the indication, with the at least one controller; generating, using the at least one RF coil, an initial MR data set for generating an initial image of the subject; determining, using the initial MR image of the subject, a difference in orientation between a current orientation of the subject in the initial MR image and a target orientation of the subject; determining, using the determined difference in orientation, an adjustment to a gradient pulse sequence for controlling the at least one gradient coil; applying the determined adjustment to the gradient pulse sequence to obtain an adjusted gradient pulse sequence; generating an adjusted MR data set using the adjusted gradient pulse sequence; and generating a second MR image of the subject using the adjusted MR data set.

As used herein, a subject may comprise a human subject, a non-human animal subject, a phantom, an agricultural product or any other suitable subject of which it is desired to obtain an MR image.

The aspects and embodiments described herein may be used individually, all together, or in any combination, as the technology is not limited in this respect.

FIG. 1 illustrates an embodiment of a system 100 for performing magnetic resonance imaging with reduced operator interaction, in accordance with some embodiments of the technology described herein. As shown in FIG. 1, the system 100 may comprise a controller 110, an MRI system 120, and a user interface 130.

The controller 110 may be configured to facilitate performance of magnetic resonance imaging with reduced operator interaction. The controller 110 may be configured to receive an indication, and in response to receiving the indication, perform a process for acquiring an MR image, as described herein. The process may comprise one or more subject loading and positioning acts, one or more acts for performing automated alignment of an MR image, and/or one or more acts for performing protocol selection, as further described herein. Accordingly, the controller 110 may comprise one or more components 112, 114, 116 for performing each act of the automated process.

The indication may comprise an interaction from a user. In some embodiments, the indication comprises an explicit input from a user to perform imaging, such as pushing a button, clicking and/or clicking an icon. In some embodiments, the indication may be implicit, such as turning on the MRI device, connecting to a network, and/or logging into a user interface.

Figure 6:
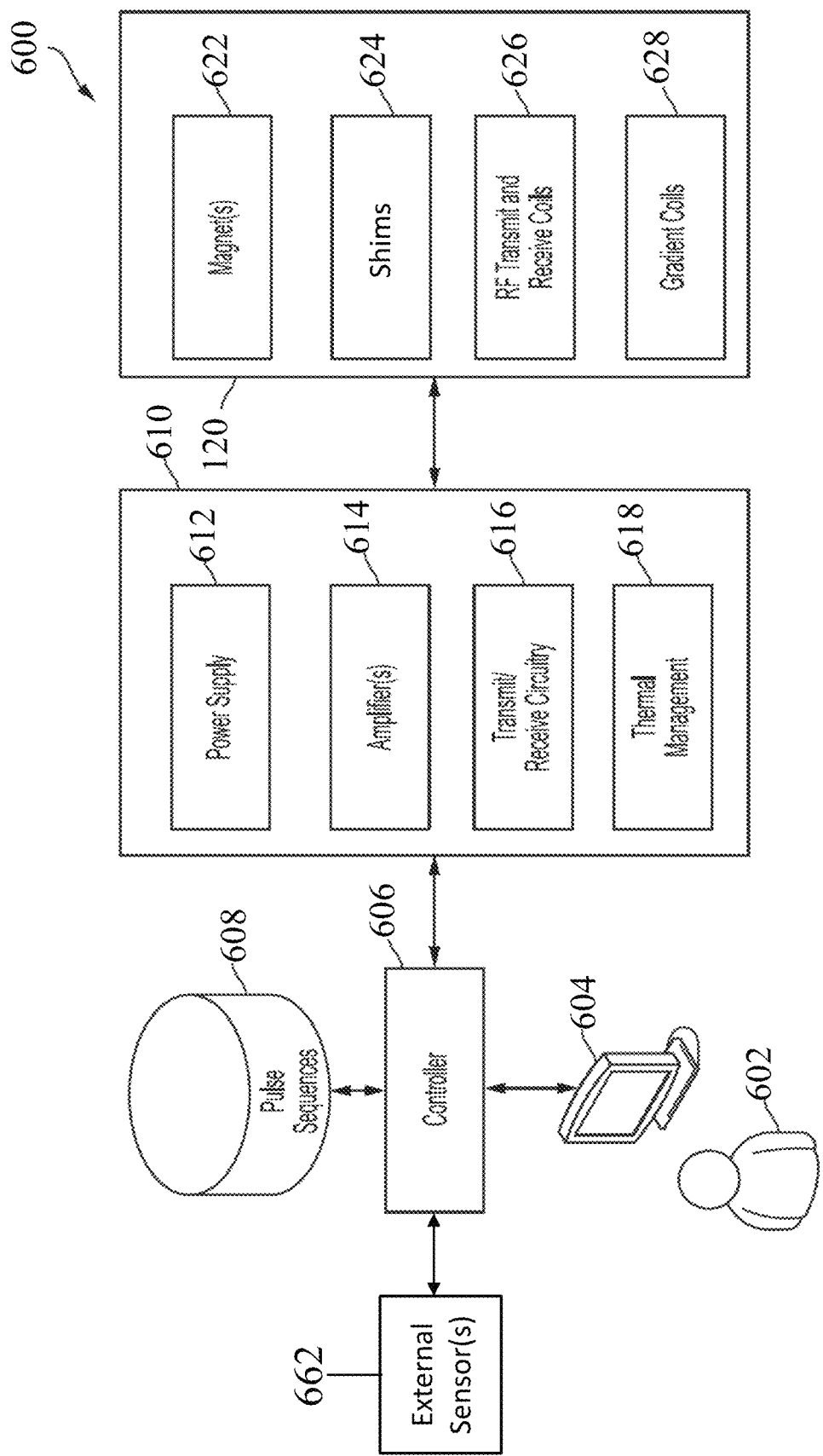
FIG. 6 illustrates an embodiment of components of a magnetic resonance imaging system, in accordance with some embodiments of the technology described herein.

The MRI system 120 may include one or more magnetics components 122 and one or more external sensors 124, as is further described herein, including with respect to FIG. 6. In some embodiments, the one or more magnetics components may comprise at least one radio-frequency coil and/or at least one gradient coil for performing MR imaging.

In some embodiments, a user may interact with the MRI system 120 via a user interface 130. The techniques described herein may allow for performing magnetic resonance imaging with reduced user interaction. Accordingly, in some embodiments, a user may initiate an MR imaging process with a single indication (e.g., a single press of a button via the user interface 130). In some embodiments, the process for MR imaging may be performed autonomously in response to the indication from the user, and may be completed without requiring further input from the user.

In some embodiments, the user interface may be on a display. The display may provide visual presentation of one or more outputs of the automated process for MR imaging described herein.

FIG. 2 illustrates a method for performing magnetic resonance imaging with reduced operator interaction 200, in accordance with some embodiments as described herein. In some embodiments, one or more of the acts of method for performing magnetic resonance imaging with reduced operator interaction 200 may be performed with at least one controller. In some embodiments, one or more acts of the method for performing magnetic resonance imaging with reduced operator interaction 200 may be performed in response to an indication without further input or interaction from a user.

In the illustrated embodiment, the method for performing magnetic resonance imaging with reduced operator interaction 200 begins with receiving an indication to image a subject using an MRI system 201. In some embodiments, the indication may comprise an input by a user (e.g., via the press of a button). In some embodiments, the indication may comprise a single input from a user. In response to receiving the indication to image the subject, one or more of performing subject loading and positioning 202, performing automated alignment of image orientation 204, selecting a protocol 206, and imaging the subject 208 may be performed autonomously. In some embodiments, each of performing subject loading and positioning 202, performing automated alignment of image orientation 204, selecting a protocol 206, and imaging the subject 208 are performed. In other embodiments, one or more of performing subject loading and positioning 202, performing automated alignment of image orientation 204, selecting a protocol 206, or imaging the subject 208 may be omitted.

The method for performing magnetic resonance imaging with reduced operator interaction 200 may comprise a number of actions that may be performed with at least one controller in response to receiving the indication to image a subject, prior to performing imaging of the subject 208. One or more of acts of the method for performing magnetic resonance imaging with reduced operator interaction 200 may comprise actions which may improve the quality of the MR image of the subject, but which may be complex and/or may require in-depth training before a user might perform such actions manually. In the illustrated embodiment, the method for performing magnetic resonance imaging with reduced operator interaction 200 proceeds to perform subject loading and positioning 202 after receiving the indication to image a subject 201 where a subject loading and positioning act may be performed. The method for performing magnetic resonance imaging with reduced operator interaction 200 then proceeds to perform automated alignment of image orientation 204 where automated alignment of image orientation may be performed. The method for performing magnetic resonance imaging with reduced operator interaction 200 then proceeds to select a protocol 206 where a protocol (e.g., a particular series of pulse sequences) may be selected. Subsequently, the method for performing magnetic resonance imaging with reduced operator interaction 200 proceeds to image the subject 208. Further aspects of subject loading and positioning 202, automated alignment of image orientation 204, and selection of a protocol 206 are described further herein.

Figure 3A:
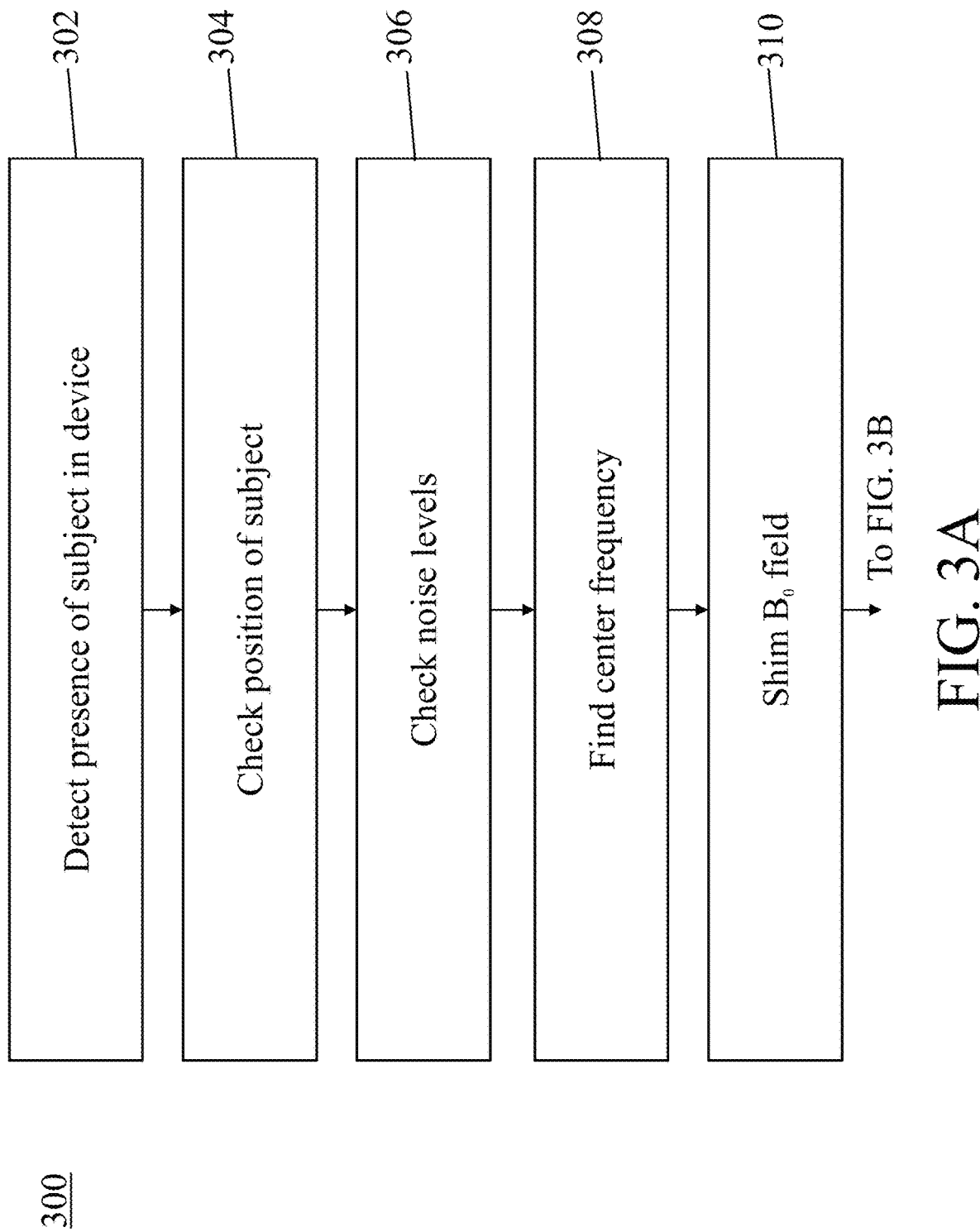
FIGS. 3A-3B illustrate an embodiment of a method for performing the subject loading and positioning act in the method of FIG. 2, in accordance with some embodiments of the technology described herein.
Figure 3B:
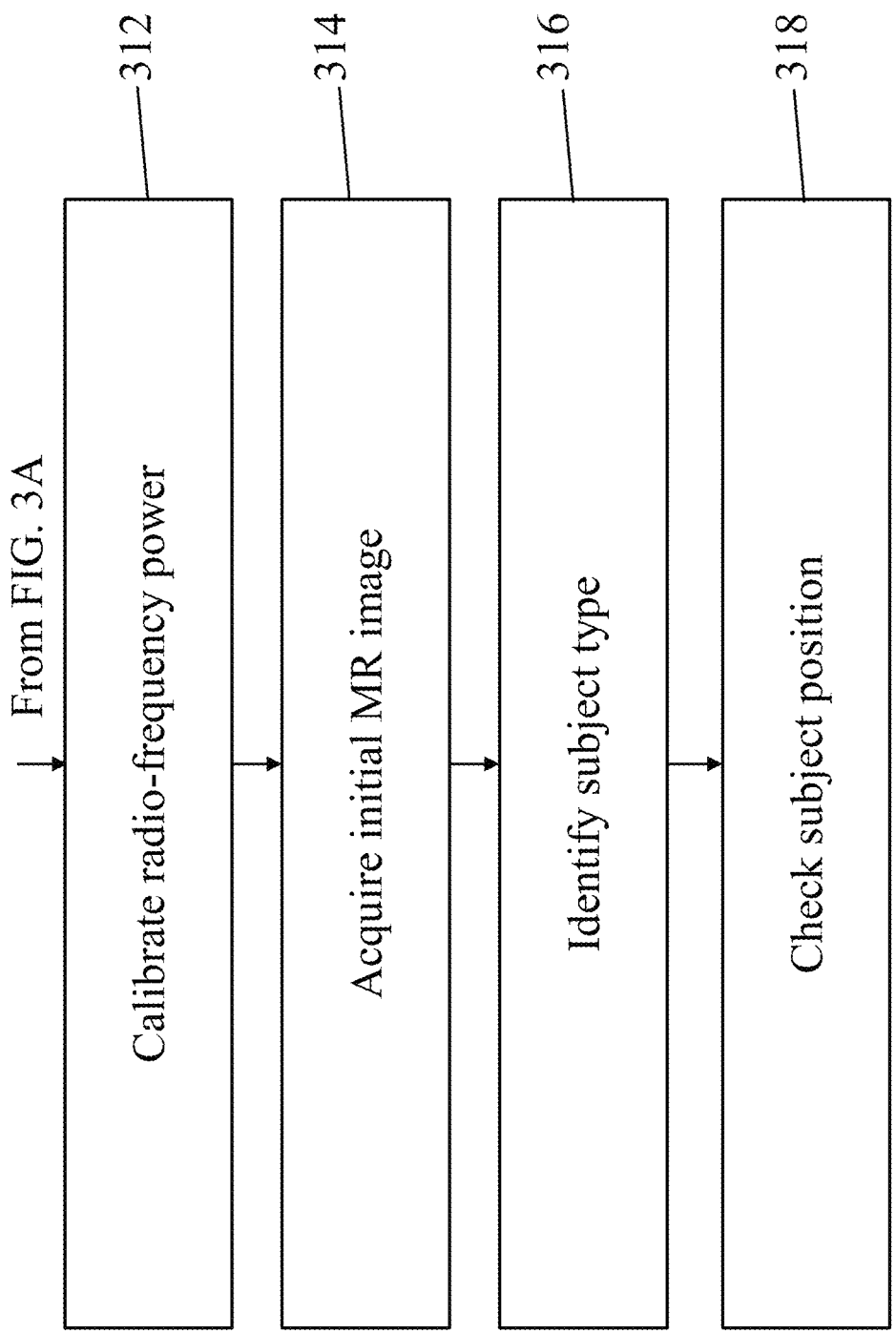

In the subject loading and positioning act, a subject may be loaded into an imaging region of the MRI system. FIGS. 3A-3B illustrate an embodiment of a method for performing subject loading and positioning 300. The subject loading and positioning act 202 of the method for performing magnetic resonance imaging 200 may include one or more of the acts described herein.

In some embodiments, the presence of a subject in the imaging region of the MRI system may be detected 302. In some embodiments, one or more sensors may be utilized to detect the presence of a subject in the imaging region.

In some embodiments, one or more optical sensors may be used to detect the presence of a subject in the imaging region of the MRI device. In some embodiments, the output from one or more optical sensors, such as a camera and/or motion sensor, may be used to determine whether a subject is present in the imaging region of the MRI device.

In some embodiments, one or more RF sensors (e.g., an RF antenna) may be utilized to detect the presence of a subject in the imaging region. The resonant frequency of a sensor (e.g., an RF sensor such as an RF antenna) may change when in the presence of a subject (e.g., a human subject, non-human animal subject, or a phantom) due to the parasitic capacitance between the sensor and the subject. The resonant frequency of the sensor may decrease as the distance between the sensor and the subject decreases. Accordingly, the presence of a subject may be detected using at least one sensor configured to capacitively couple with the subject.

In some embodiments, presence of a subject is detected using magnetic resonance. In some embodiments, a magnetic resonance signal may be obtained by performing a process for magnetic resonance imaging. In particular one or more radio frequency pulses may be transmitted by at least one radio-frequency coil and the MR signals emitted in response may be detected by the at least one radio-frequency coil. Based on the detection of MR signals by the at least one radio-frequency coil, it may be determined that a subject is present in the imaging region. In some embodiments, one or more images of the subject are acquired using the process for magnetic resonance imaging. The one or more images may be low resolution MR images. The one or more images may be fit to a template to determine whether a subject is present in the imaging region of the MRI system based on whether a subject is present in the MR image.

If, it is detected that the subject is not present in the imaging region of the device, an indication may be presented to a user of this result. In some embodiments, an indication, such as a visual or audial indication via a user interface may be provided to notify the user that the presence of a subject in the imaging region is not detected and manual intervention may be required.

In some embodiments, a position of the subject in the device may be assessed 304, which may include determining if the subject is improperly positioned. In some embodiments, the position of the subject is assessed using one or more optical sensors (e.g., one or more cameras), one or more pressure sensors, one or more RF sensors (e.g., one or more RF antennas), and/or any other suitable sensor.

In some embodiments, one or more MR images are obtained. To assess the position of the subject relative to the MRI system, a mask over the image may be computed. The image may be divided into a number of images, and the presence of the subject in each of the slices may be detected by determining whether each slice contains signal. In some embodiments, the MRI system may comprise one or more RF coil assemblies such as a head coil. Assessing the position of the anatomy may include assessing the position of the anatomy in the RF coil assembly.

In some embodiments, a visual of the planned imaging field of view and the current position and/or orientation of the subject may be presented to the user (e.g., via the user interface). In some embodiments, the planned imaging field is shown with the corrected alignment, as described herein. In some embodiments, the planned imaging field is shown without the corrected alignment.

In some embodiments, a user may be notified if it is determined that the subject is improperly positioned. In some embodiments, if it is determined that less than a threshold percentage (e.g., 75%) of the slices contain signal, it may be determined that the subject is improperly positioned and the user may be notified. In some embodiments, instructions may be generated instructing the user how the subject should be repositioned (e.g., instructing the user to move the subject farther into the imaging region of the MRI system).

Figure 9:
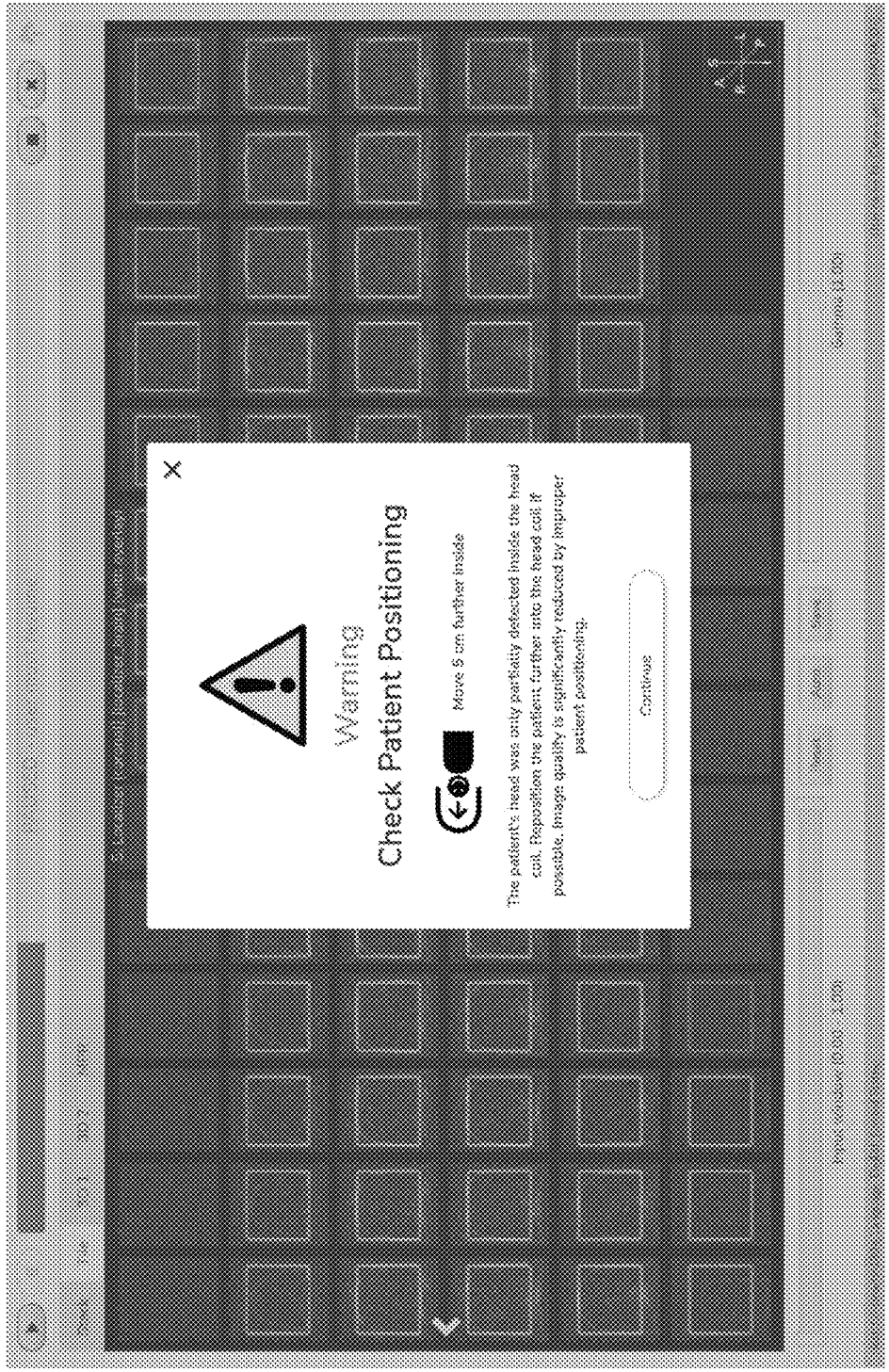
FIGS. 9-11 illustrate embodiments of user interfaces, in accordance with some embodiments of the technology described herein.

FIG. 9 illustrates an embodiment of a user interface. In some embodiments, the user interface of FIG. 9 may be used with the method of FIGS. 3A-3B, in accordance with some embodiments of the technology described herein. As shown in FIG. 9, a user interface presents a warning that the subject may be improperly positioned and provides and instruction on how to adjust the subject's position to improve image quality.

Assessing the position of the patient may be performed one or more times. In some embodiments, the autonomous process includes one or more calibration acts, as described herein. It may be advantageous to perform the one or more calibration acts, such as shimming the $B_0$ magnetic field generated by the MRI system, when the subject is properly positioned (e.g., in substantially the same position the subject will be in when MR imaging is performed). Still, it may be advantageous to assess position after the calibration acts have been performed. In some embodiments, assessing the subject's position may be facilitated via use of MR signals and/or images. Accordingly, in some embodiments, the autonomous process includes at least one act for assessing the subject's position performed subsequent to one or more calibration acts.

In some embodiments, noise levels in the environment of the MRI system may be assessed 306. Any suitable technique for measuring noise may be used. In some embodiments, a camera may be used to identify hospital equipment which may cause interference with the MRI system and their proximity to the MRI system. In some embodiments, one or more foreign objects in the environment of the MRI system (e.g., jewelry, electronic devices) may be identified. In some embodiments, one or more other MRI systems may be identified.

In some embodiments, the noise level may be compared to a threshold value. If it is determined that the noise level in the environment of the MRI system is too high (e.g., by determining the noise level exceeds the threshold value), the user may be notified and/or instructed (e.g., via the user interface) to reduce interference through one or more actions (e.g., removing one or more foreign objects, powering off one or more electronics, such as an LCD display, distancing interfering objects from the MRI system, determining if one or more shielding components such as an RF screen has been properly implemented etc.). A subsequent assessment of the noise levels in the environment of the MRI system may be performed after the user has been instructed to take action to reduce interference. In some embodiments, data collected regarding the noise level in the environment of the MRI system may be stored for later use in image reconstruction, when generating the MR image.

In some embodiments, a center frequency of the MRI system may be found 308. In some embodiments, a free induction decay (FID) sequence may be performed by the MRI system. The resulting signal received in response to the FID sequence may transformed to the frequency domain. Based on this measurement, the frequency corresponding to the peak signal may be determined. If a center frequency cannot be found, the user may be instructed (e.g., via the user interface) to take one or more subsequent actions (e.g., reloading the subject into the imaging region of the MRI system, checking coil connections of MRI system components). A subsequent assessment of the center frequency may be performed after the user has been instructed to take action. Checking for a center frequency may be repeated until a center frequency is found.

In some embodiments, the $B_0$ magnetic field generated by the MRI system may be shimmed 310. In some embodiments, the MRI system may be operated to obtain two MR images with different echo times (e.g., a first MR image having a first echo time and a second MR image having a second echo time different than the first echo time). The phase difference of the two images, which is proportional to the $B_0$ field generated by the MRI system, may be computed. The computed phase difference may be fit to a three-dimensional linear model (e.g., a linear harmonic decomposition) to obtain x, y, and z shims that can be applied to negate the impact of the linear magnetic field inhomogeneities. Such inhomogeneities may be compensated by applying current offsets to one or more of the gradient coils of the MRI device.

In some embodiments, a power of the radio-frequency components (e.g., the one or more radio-frequency coils, as described herein) may be calibrated 312. In some embodiments, a free induction decay (FID) sequence may be performed by the MRI system to excite the volume of the imaging region. The RF power of the FID sequence (e.g., the amplitude of the excitation pulse) may vary from zero to a maximum. The profile of the resulting MR signal received in response to the FID sequence may be fit to a model of the signal to determine the power needed to obtain a peak bi field produced by the RF components of the MRI system. In some embodiments, the resulting signal may be plotted against RF power amplitude. The power required for a given flip angle (e.g., 90 or 180 degrees) and/or the power required to power one or more passive diodes coupled to transmit circuitry of the MRI device (e.g., a transmit RF coil) may be determined based on the plot.

In some embodiments, an initial MR image may be obtained 314. The initial MR image may comprise a localizer image, also referred to as a scout image. The initial MR image may be an image separate from the imaging of the subject 208 of the method for performing magnetic resonance imaging with reduced operator interaction 200. The initial MR image may be used to assist with subject positioning, including any required orientation correction. In some embodiments, the initial MR image may be of a low resolution. In some embodiments, a short PSIF (reverse fast imaging with steady-state free precession) sequence having a T2 contrast which approximately matches a template image, as described herein, may be performed by the MRI system to obtain the initial MR image.

In some embodiments, a type of the subject may be identified 316 based on the initial MR image. Identifying the subject type may comprise identifying the subject as one of a human subject, a non-human animal subject, or a phantom, in some embodiments. In some embodiments, identifying the subject type may comprise identifying a portion of the subject anatomy (e.g., a head, foot, knee, etc.) that is to be imaged.

In some embodiments, the initial MR image obtained at act 314 may be used to identify the subject type. In some embodiments, the initial MR image may be compared to a template image (e.g., a template MR image) of a possible subject type (e.g., possible subject anatomy) with matched contrast. In some embodiments, the template image may comprise a composite image comprising multiple scans (e.g., from one or more subjects) of a same anatomy. A measure of the goodness of fit of the initial MR image to the template image may be performed to identify whether the initial MR image matches the template image. Based on the comparison, the subject type may be identified including whether the subject comprises a human subject, a non-human animal subject, or a phantom and/or what portion of the body the anatomy is.

In some embodiments, information about the at least one RF coil used to obtain the initial MR image may be used to identify the subject type. In some embodiments, an ID associated with an RF coil, such as an RF coil used to obtain the initial MR image, an RF coil which has detected an MR signal, and/or an RF coil which is currently being supplied with power, may be used to identify the subject type. In some embodiments, if the coil ID matches that of an RF coil apparatus configured to image a particular subject anatomy (e.g., a head coil configured to image a head), the subject type may be identified as the particular subject anatomy that the RF coil apparatus corresponding to the coil ID is configured to image. In some embodiments, the information about the at least one RF coil may be used in combination with the initial MR image to identify the subject type. In some embodiments, the template image may be selected based on an ID associated with the particular RF coil that is used to obtain the initial MR image.

In some embodiments, the position of the subject may be checked 318. In some embodiments, the position of the subject may be assessed based on the initial MR image. Use of MR data and/or an MR image may provide for a highly accurate technique for assessing a position of the subject. As described herein, when MR data and/or an MR image is used to assess subject position, it may be advantageous to acquire the MR image used to assess subject position subsequent to performing one or more calibration acts.

In some embodiments, as described herein, a mask over the initial MR image may be computed. The mask may correspond to a desired position of the subject. The initial MR image may be divided into a number of sub-images (e.g., slices), and the presence of the subject in each of the slices may be detected by determining whether each slice contains signal. In some embodiments, it may be determined that the subject should be repositioned based on a percentage of slices which contain signal. In some embodiments, where a percentage of slices expected to contain signal is below a threshold (e.g., 75%), repositioning the subject may be recommended.

In some embodiments, the initial MR image may be compared to a template image illustrating the subject in a desired position. A distance representing a deviation from the desired position may be determined based on a comparison between the initial MR image and the template image. The distance out of position relative to the total dimensions of the image may be calculated to obtain a obtain a distance, direction, and/or rotation in which the subject is out of position (e.g. where the subject is 2 cm out of position along a first axis and the imaging field of view is 20 cm wide along the first axis). In another embodiment the distance and direction out of position may be determined based on a subset of the anatomy to be imaged. (e.g. to position anatomy of a joint such as a knee or elbow in the center of the imaging field of view). In some embodiments, it may be determined that the subject should be repositioned based the determined distance and/or percentage in which the subject is out of position. In some embodiments, where the distance and/or percentage is above a threshold (e.g., 10%), repositioning the subject may be recommended.

In some embodiments, the identified subject type may be used to facilitate assessing the subject position. In some embodiments, the subject type may be used to determine which template images are compared to the initial MR image when assessing subject position. Accordingly, the comparison may be simplified by reducing the number of template images which may be compared to the initial MR image to assess subject position.

In some embodiments, based on the assessment of the position of the subject, the user may be instructed to make adjustments to the position of the subject. In some embodiments, instructions may be provided to the user (e.g., via the user interface) on how to adjust the subject's position. In some embodiments, subsequent to any changes in the anatomy's position, the method for performing patient loading and positioning 300 may return to acquire an additional MR image 314 (e.g., a localizer image) and/or to identify the subject type 316 to reassess the subject's position.

The acts described herein may be performed in any suitable order. It should be appreciated that one or more of the acts described herein related to subject loading and positioning may be optional and, in some embodiments, performing subject loading and positioning may not include all of the acts described herein. In addition, performing subject loading and positioning may comprise one or more additional acts in some embodiments. In some embodiments, the initial MR image may be used to detect foreign objects (e.g., jewelry, electronics) in the imaging region. The presence of signal void may indicate the possibility of foreign objects being present in the imaging region. The user may subsequently be alerted to inspect the subject for such foreign objects when a foreign object is detected. In some embodiments, one or more coils may be tuned prior to imaging. In some embodiments, the process may include tuning the radio-frequency coil (e.g., the transmit RF coil) to a center frequency prior to performing imaging.

In the automated alignment act of the method for performing magnetic resonance imaging with reduced operator interaction 200, the orientation of the subject may be assessed. In particular, a current orientation of the subject may be compared to a target orientation and a difference between the current orientation of the subject and the target orientation may be determined. In some embodiments, the difference in orientation may be corrected without requiring further input or action from a user.

Figure 4:
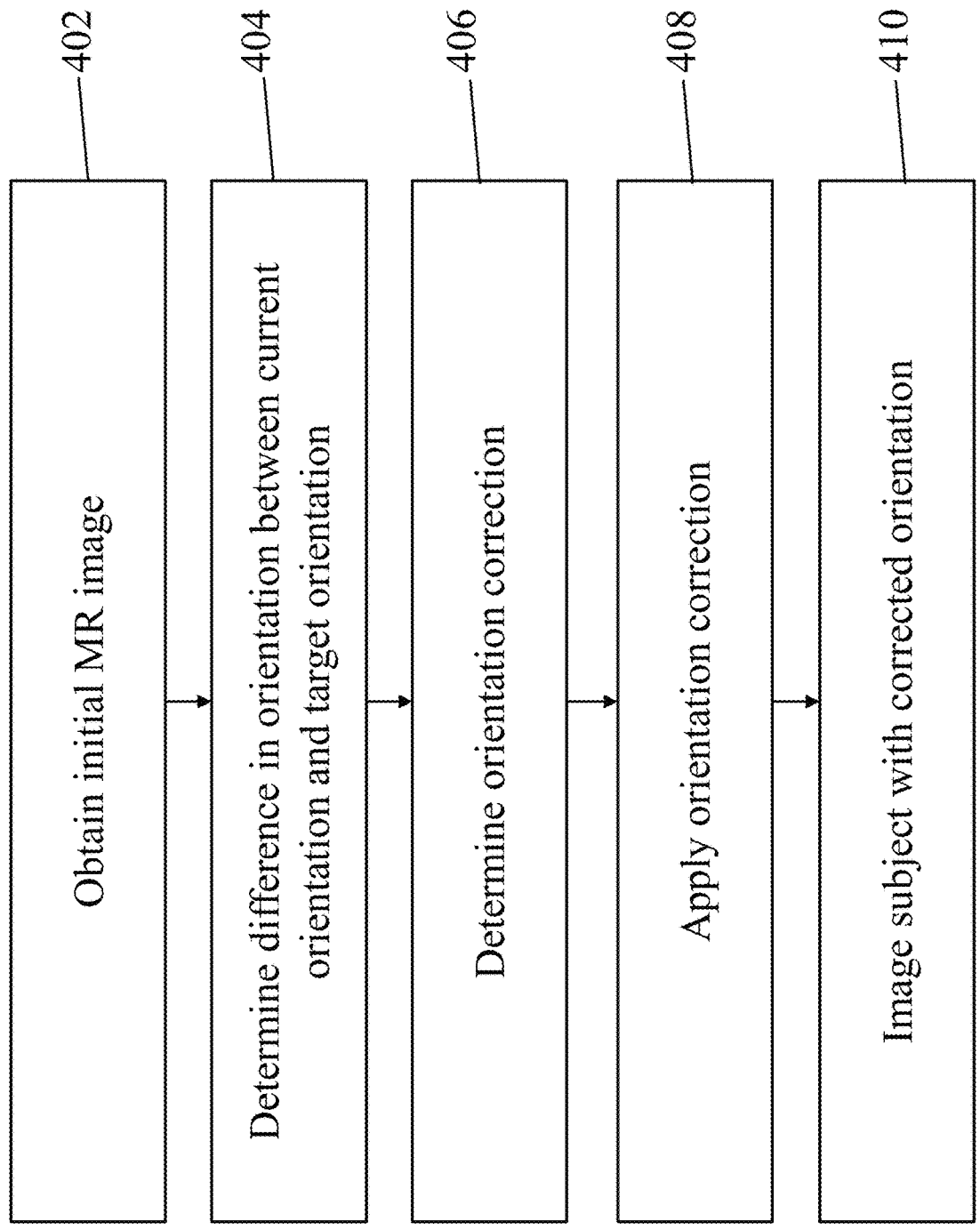
FIG. 4 illustrates an embodiment of a method for performing the automated alignment of image orientation act in the method of FIG. 2, in accordance with some embodiments of the technology herein.

FIG. 4 illustrates an embodiment of a method for performing the automated alignment of image orientation act in the method of FIG. 2, in accordance with some embodiments of the technology herein. The automated alignment of image orientation act 204 of the method for performing magnetic resonance imaging with reduced operator interaction 200 may include one or more of the acts of the method for performing automated alignment of image orientation 400. In some embodiments, the method for performing automated alignment of image orientation 400 may be performed with at least one controller subsequent to performing one or more of the acts of method for performing subject loading and positioning 300. In other embodiments, the method for performing automated alignment of image orientation 400 may be performed in response to an indication to image a subject without performing the method for performing subject loading and positioning 300.

The method for performing automated alignment of image orientation 400 may begin by acquiring an initial MR image of the subject 402. In some embodiments, the initial MR image may comprise a localizer image, also referred to as a scout image. The initial MR image may be an image separate from the imaging performed at the imaging act 208 of the method for performing magnetic resonance imaging with reduced operator interaction 200. In some embodiments, the initial MR image may be of a low resolution. In some embodiments, a short PSIF (reverse fast imaging with steady-state free precession) sequence having a T2 contrast which approximately matches a template image, as described herein, may be performed by the MRI system to obtain the initial MR image.

If an initial MR image has already been obtained, no additional initial MR images may be obtained, in some embodiments. In some embodiments, an additional initial MR image may be obtained in the method for performing automated alignment of image orientation 400 to supplement the initial MR image previously obtained.

In some embodiments, a difference in orientation between a current orientation of the subject and a target orientation may be determined 404. In some embodiments, the difference in orientation may be determined by comparing the initial MR image to a template image having the subject in the target orientation. A difference in orientation between the current orientation as shown in the initial MR image and the target orientation as shown in the template image may be determined based on the comparison.

In particular, the difference in orientation of the subject in the initial MR image and the template image may be determined using a registration method such as a rigid, affine, and/or non-rigid registration. The registration may reflect changes in an image by one or more factors including translation, rotation, scaling, and/or reflection. For the purposes of determining a change in orientation, the change in rotation between the images as reflected by the registration may be isolated to determine the difference in orientation between the current orientation of the subject and the target orientation of the subject. In some embodiments, the difference in orientation may be computed by isolating and registering features in the initial MR image and the template MR image (e.g. aligning the initial MR image and the template MR image based on specific bone landmark structures). The changes in orientation may be determined about multiples axes, such as three substantially perpendicular axes (e.g., roll, pitch, and/or yaw), in some embodiments.

In some embodiments, the difference in orientation may be determined based on a difference between a portion of the initial MR image and a portion of the template MR image. In some embodiments, the portion of the initial MR image and the portion of the template MR image may comprise a set of points in the respective images and the position of the respective points of the set of points may be compared between the initial MR image and the template MR image to determine the difference in orientation.

In some embodiments, an orientation correction may be determined 406. As described herein, the method for automated alignment of image orientation 400 may correct for a difference in orientation of a subject from a target orientation without requiring the user to provide input or perform any manual intervention. The orientation correction may comprise parameters which automatically compensate for the difference in orientation.

In some embodiments, the orientation correction comprises an adjustment to one or more gradient pulse sequences for performing gradient pulses during MR imaging. In some embodiments, using the determined difference in orientation, rotations may be applied to the gradient pulses at compile time to align the image to the subject anatomy.

In some embodiments, if an axial head scan is to be performed, but the subject's head is rotated, the scanner gradient coordinate system may be rotated so that the head appears in the correct axis orientation in the acquired images (instead of requiring the user to adjust the position of the anatomy manually).

More particularly, the method may include rotating a frame of reference of the gradient waveform. Rotating the frame of reference of the gradient waveform may be performed, by applying a transformation (e.g., a rotation) to the gradient waveform (e.g., by applying a rotation matrix to the gradient waveform). A transform representing the rotation to be applied to the gradient waveform may be estimated from the template MR image (a set of data which may be reflected by $x_2$) and the initial MR image (a set of data which may be reflected by $x_1$). In some embodiments, the transformation may be a rigid transformation comprising a rotation R matric and a translation vector t such that: $x_2=Rx_1+t$, and estimating the transformation may comprise estimating the values of R and t (e.g., assuming 6 degrees of freedom) from the data in the template MR image and the initial MR image so that the above equation is satisfied as closely as possible under a suitable choice of metric (correlation, mean-squared error, l1-norm, a regularized norm, etc.). It should be appreciated, however, that in some embodiments, the transformation need not be limited to a rigid transformation and may be any other suitable type of transformation, as aspects of the technology described herein at not limited in this respect.

In some embodiments, the orientation correction additionally or alternatively comprises an adjustment to one or more RF pulse sequences for transmitting RF pulses during MR imaging. In some embodiments, using the difference in orientation determined at act 406, rotations may be applied to the RF pulses at compile time to align the image to the subject anatomy. In some embodiments, one or more RF pulse sequences may be adjusted when the pulse sequence is slice selective (e.g., imaging 2D slices individually) or otherwise spatially selective. In some embodiments, one or more RF pulse sequences may be adjusted when the RF pulse sequence is designed to compensate for a property of the MRI device, such as $B_0$ and/or RF field inhomogeneity.

In some embodiments, the determined orientation correction may be applied 408. In some embodiments, applying the orientation correction may comprise applying the adjustment to the one or more gradient pulse sequences to obtain an adjusted gradient pulse sequence. Performing the adjusted gradient pulse sequence compensates for the difference in orientation between the current orientation of the subject and the target orientation without requiring the user to manually reposition the subject. Accordingly, the orientation correction facilitates performing magnetic resonance imaging with reduced user interaction.

In some embodiments, the subject may be imaged with the corrected orientation 410. In some embodiments, imaging the subject with the corrected orientation may comprise performing the adjusted gradient pulse sequence.

In some embodiments, the method for performing automated alignment of image orientation may comprise applying the determined orientation correction during image reconstruction (e.g., when generating an MR image based on data collected during imaging of the subject). In some embodiments, a model of gradient non-linearity and $B_0$ inhomogeneity may be used to calculate a correction to geometrically unwarp images. In such embodiments, the unwarping model may be corrected for adjustments applied to the gradient pulse sequence due to the difference in orientation.

In some embodiments, during image reconstruction, an MR image may be corrected for RF transmit and/or receive coil sensitivity. Such coil sensitivity models may be corrected, by rotating and adjusting the sensitivity models, based on the adjustments to gradient and/or RF pulse sequences due to the difference in orientation. In some embodiments, correction for coil sensitivity may be based on pre-calibrated models. Such pre-calibrated models may be rotated and/or translated in the manner that the gradient and/or pulse sequences are adjusted based on the difference in rotation.

Figure 10:
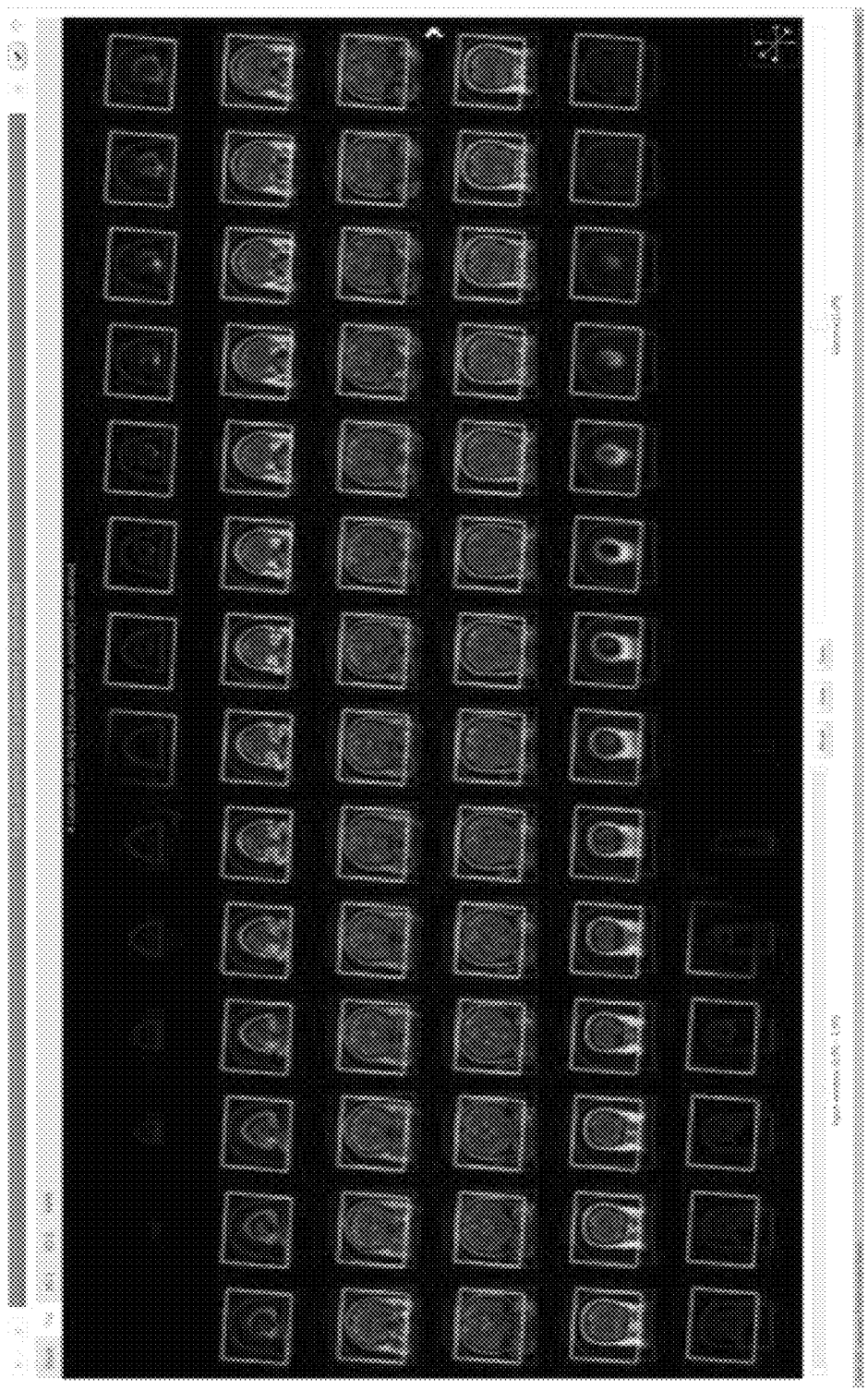
Figure 11:
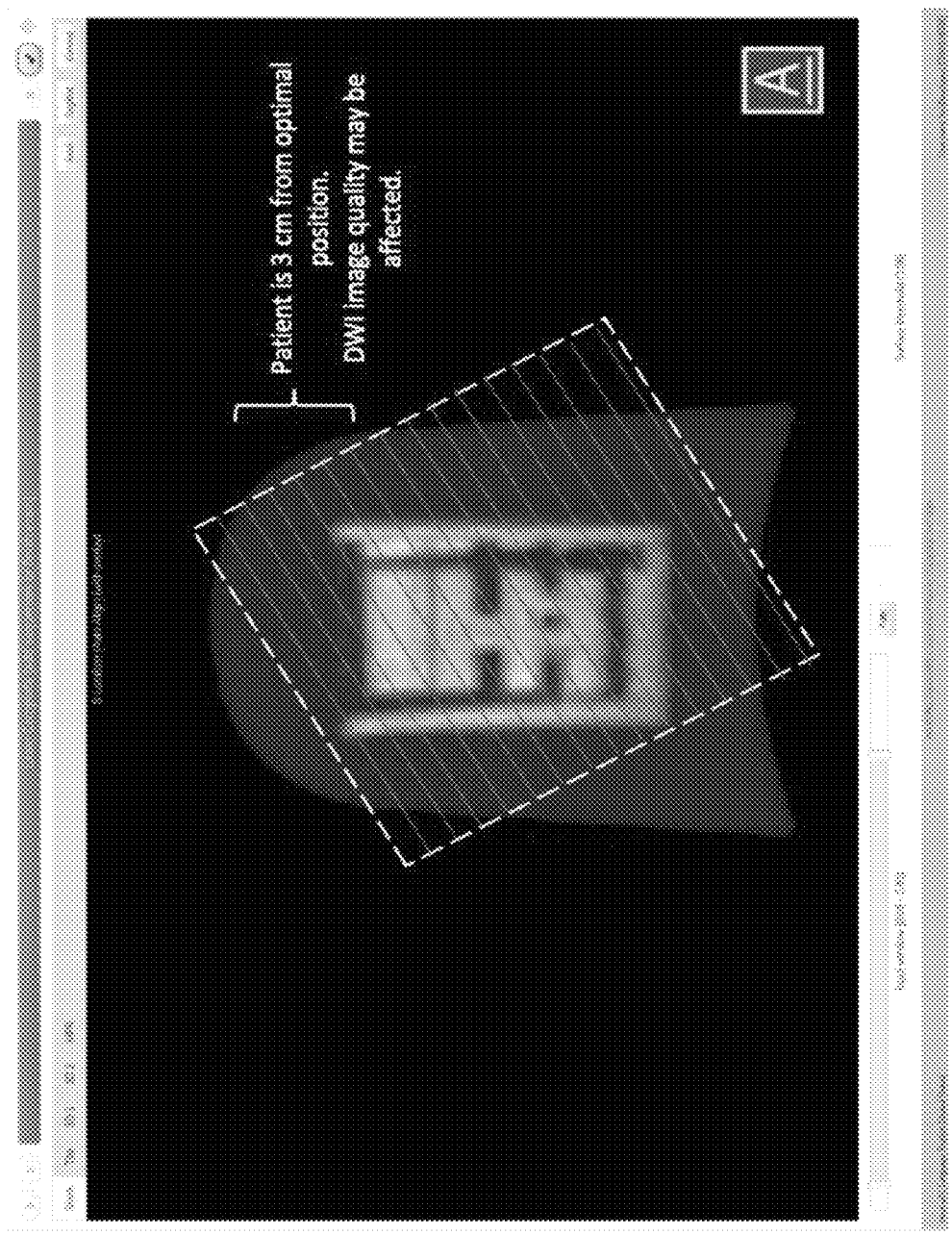

FIGS. 10-11 illustrate embodiments of user interfaces, The user interfaces may be used with the method of FIG. 4, in accordance with some embodiments of the technology described herein. FIG. 10 illustrates an embodiment of an initial MR image having overlaid the target orientation (e.g., the intended scan field of view). In some embodiments, the interface of FIG. 10 may be displayed to a user during the performance of the automated alignment of image orientation act. FIG. 11 is another embodiment of an interface illustrating an embodiment of an initial MR image. In FIG. 11, a single slice is shown. An outline of the radio-frequency coil used to obtain the initial MR image is shown in FIG. 11. FIG. 11 includes an embodiment of an indication to the user regarding the subject's position and potential impact on image quality.

Figure 5:
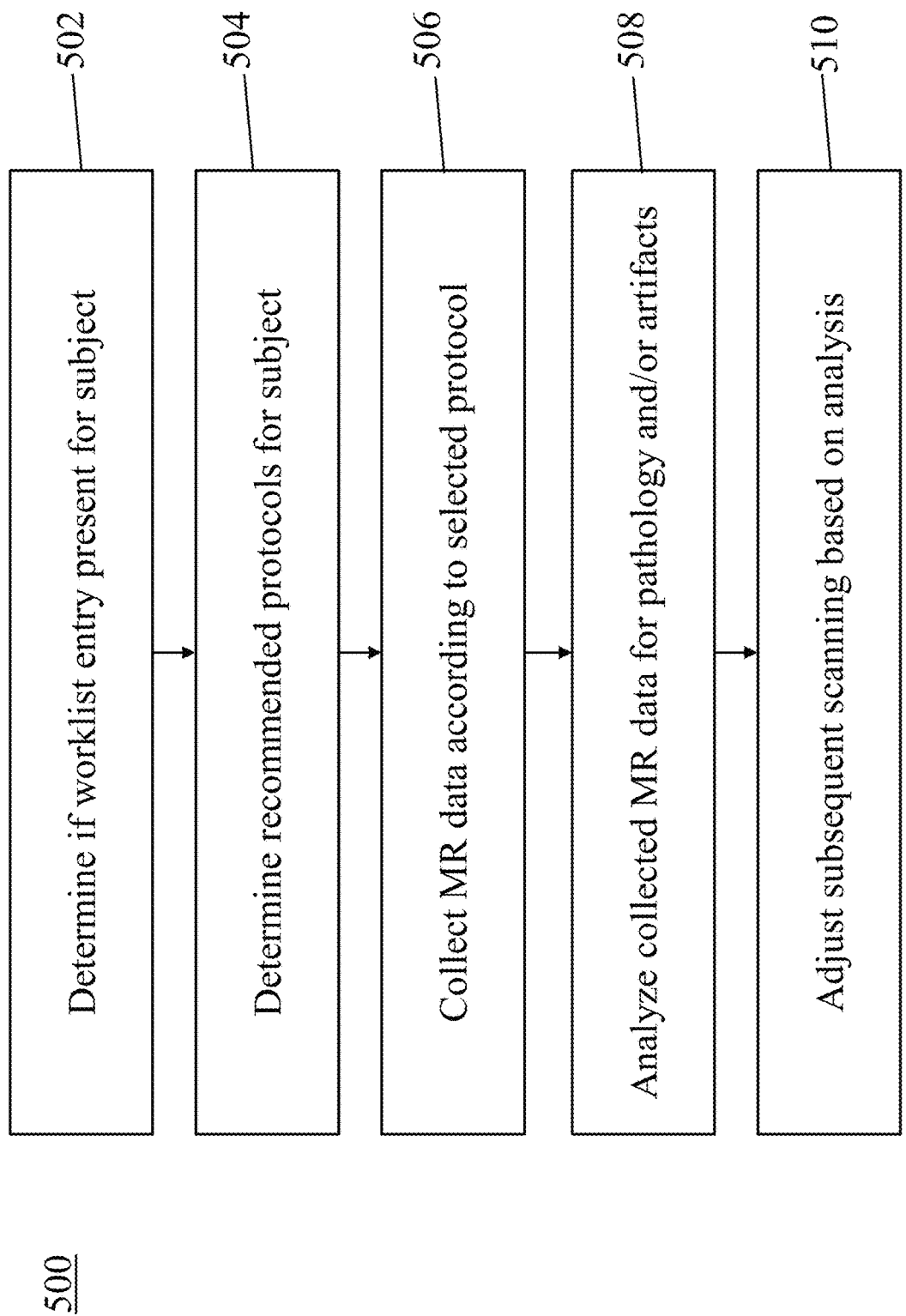
FIG. 5 illustrates an embodiment of a method for performing the protocol selection act in the method of FIG. 2, in accordance with some embodiments of the technology herein.

In the protocol selection act of the method for performing magnetic resonance imaging with reduced operator interaction 200, a series of pulse sequences for use in performing an MR image acquisition may be selected. FIG. 5 illustrates an embodiment of a method for performing the protocol selection 500, in accordance with some embodiments of the technology herein. The method for performing magnetic resonance imaging with reduced operator interaction 200 may include one or more of the acts of the method for performing protocol selection 500. In some embodiments, the method for performing protocol selection 500 may be performed subsequent to one or more acts of one or both of the method for performing subject loading and positioning 300 and the method for performing automated alignment of image orientation 400.

In some embodiments, it may be determined if there is a worklist entry present for the subject 502. In one embodiment, the MRI system may determine if there is a worklist entry present for the subject by scanning (e.g., using an optical sensor, such as a camera) a barcode attached to the subject (e.g., on a bracelet, on the subject's clothing, etc.). The worklist entry may indicate a particular protocol to be used for imaging the subject (e.g., past protocols used for the particular subject). In some embodiments, the worklist entry may indicate one or more characteristics of the subject which may be used to assist in determining a recommended protocol to be used for imaging the subject (e.g., one or more medical conditions of the subject).

In some embodiments, one or more recommended protocols for use in imaging the subject may be determined 504. In some embodiments, the one or more recommended protocols may be selected using the worklist entry, if present, the identified subject type including the identified subject anatomy and/or the determination of whether the anatomy is of a human subject, a non-human animal subject, or a phantom, and/or the determined orientation of the anatomy. In some embodiments, if the anatomy is determined to be a brain, the system may include T1, T2, FLAIR, and DWI pulse sequences in a list of recommended protocols. In some embodiments, where the anatomy is determined to be a knee, the system may include proton density (PD) and fat-suppressed imaging (STIR) sequences to be includes in a list of recommended protocols. If the anatomy is determined to be a phantom, one or more quality assurance protocols may be recommended. In some embodiments, the system may generate recommended protocols based on a subject's age and/or a pathology associated with the subject.

In some embodiments, the MRI system may be configured to select one or the one or more recommended protocols to begin imaging the subject according to the selected protocol. In some embodiments, the one or more recommended protocols may be used to generate a list of recommended protocols that are presented to the user for selection and the MRI system may begin imaging the subject according to the protocol selected by the user. Accordingly, a user interface presenting a list of available protocols may be simplified for an untrained user by reducing the number of available protocols for selection. In other embodiments, the recommended protocol may be automatically performed without requiring input from a user.

In some embodiments, MR data of the anatomy may be collected according to the selected protocol 506. In some embodiments, collecting MR data according to the selected protocol 506 may comprise performing one or more pulse sequences of the selected protocol and collecting MR signals emitted in response to the one or more pulse sequences.

In some embodiments, the collected MR data may be analyzed for pathology and/or artifacts 508. In some embodiments, analyzing the collected MR data may be performed dynamically, prior to completion of the protocol.

In some embodiments, collected MR data may be analyzed dynamically to determine whether to reacquire data or acquire additional data. The collected MR data may indicate the presence of one or more artifacts (e.g., motion, noise) during imaging that can be reduced or eliminated by reacquiring data and/or acquiring additional data.

In some embodiments, collected MR data may be analyzed to detect a pathology. The detected pathology and confidence detection of the detected pathology maybe displayed in real time. Based on the identified pathology, one or more subsequent actions may be performed 510 (e.g., prescribing additional scans).

In some embodiments, if an axial FLAIR (fluid-attenuated inversion recovery) sequence detects white matter lesions, a sagittal FLAIR sequence may be prescribed and/or a recommendation to evaluate potential multiple sclerosis may be made. The MRI system may perform such subsequent actions in response to the pathology detection. In some embodiments, the MRI system may perform the subsequent actions without further input or interaction from a user.

In some embodiments, if a scan is being performed for a potential stroke (e.g., based on a worklist entry), the MRI system may select a diffusion weighted imaging (DWI) and apparent diffusion coefficient (ADC) sequence, followed by a FLAIR sequence. If both scans are negative the scanning can stop. If one or both of the scans are positive, subsequent T2 and T1 scans may be prescribed. In some embodiments, if the DWI scan is positive and the FLAIR scan is negative (such as in the case of an acute stroke), the MRI system may predict the presence of a large vessel occlusion (LVO) stroke and subscribe subsequent scanning using magnetic resonance angiography (MRA).

In some embodiments, the pathology detection may initiate changes to the protocol workflow. In some embodiments, a positive pathology scan may trigger transmitting collected images to a picture archiving and communication system (PACS). In some embodiments, a positive pathology detection may trigger one or more notifications to be sent. In some embodiments, a positive pathology detection may initiate triaging of scans for a radiology reading. In some embodiments, the pathology detection may trigger changes to the ordering and/or number or remaining pulse sequences to be performed (e.g., adding or removing scans from the selected protocol).

FIG. 6 illustrates exemplary components of an MRI system which may be used to perform at least some, or all of the techniques described herein. In the illustrated embodiment of FIG. 6, an MRI system 600 comprises a computing device 604, a controller 606, a pulse sequences repository 608, a power management system 610, and a magnetics components 620. It should be appreciated that the MRI system 600 is illustrative and that an MRI system may have one or more other components of any suitable type in addition to or instead of the components illustrated in FIG. 6. However, an MRI system will generally include these high-level components, though the implementation of these components for a particular MRI system may differ.

As illustrated in FIG. 6, the magnetics components 620 comprise $B_0$ magnets 622, shims 624, radio frequency (RF) transmit and receive coils 626, and gradient coils 628. The $B_0$ magnets 622 may be used to generate the main magnetic field $B_0$. The $B_0$ magnets 622 may be any suitable type or combination of magnetics components that can generate a desired main magnetic $B_0$ field. In some embodiments, the $B_0$ magnets 622 may be one or more permanent magnets, one or more electromagnets, one or more superconducting magnets, or a hybrid magnet comprising one or more permanent magnets and one or more electromagnets and/or one or more superconducting magnets. In some embodiments, the $B_0$ magnets 622 may be configured to generate a $B_0$ magnetic field having a field strength that is less than or equal to 0.2 T or within a range from 50 mT to 0.1 T (e.g., greater than and/or equal to 50 mT and less than and/or equal to 0.1 T).

In some embodiments, the $B_0$ magnets 622 may include a first and second $B_0$ magnet, each of the first and second $B_0$ magnet including permanent magnet blocks arranged in concentric rings about a common center. The first and second $B_0$ magnet may be arranged in a bi-planar configuration such that the imaging region is located between the first and second $B_0$ magnets. In some embodiments, the first and second $B_0$ magnets may each be coupled to and supported by a ferromagnetic yoke configured to capture and direct magnetic flux from the first and second $B_0$ magnets.

The gradient coils 628 may be arranged to provide gradient fields and, in some embodiments, may be arranged to generate gradients in the $B_0$ field in three substantially orthogonal directions (X, Y, Z). The gradient coils 628 may be configured to encode emitted MR signals by systematically varying the $B_0$ field (the $B_0$ field generated by the $B_0$ magnets 622 and/or the shims 624) to encode the spatial location of received MR signals as a function of frequency or phase. In some embodiments, the gradient coils 628 may be configured to vary frequency or phase as a linear function of spatial location along a particular direction, although more complex spatial encoding profiles may also be provided by using nonlinear gradient coils. In some embodiments, the gradient coils 628 may be implemented using laminate panels (e.g., printed circuit boards).

MRI is performed by exciting and detecting emitted MR signals using transmit and receive coils, respectively (often referred to as radio frequency (RF) coils). Transmit/receive coils may include separate coils for transmitting and receiving, multiple coils for transmitting and/or receiving, or the same coils for transmitting and receiving. Thus, a transmit/receive component may include one or more coils for transmitting, one or more coils for receiving and/or one or more coils for transmitting and receiving. Transmit/receive coils are also often referred to as Tx/Rx or Tx/Rx coils to generically refer to the various configurations for the transmit and receive magnetics component of an MRI system. These terms are used interchangeably herein. In FIG. 6, RF transmit and receive coils 626 comprises one or more transmit coils that may be used to generate RF pulses to induce an oscillating magnetic field Bi. The transmit coil(s) may be configured to generate any suitable types of RF pulses.

The power management system 610 includes electronics to provide operating power to one or more components of the MRI system 600. In some embodiments, the power management system 610 may include one or more power supplies, energy storage devices, gradient power components, transmit coil components, and/or any other suitable power electronics needed to provide suitable operating power to energize and operate components of the MRI system 600. As illustrated in FIG. 6, the power management system 610 comprises a power supply system 612, power component(s) 614, transmit/receive circuitry 616, and thermal management components 618 (e.g., cryogenic cooling equipment for superconducting magnets, water cooling equipment for electromagnets).

The power supply system 612 includes electronics to provide operating power to magnetic components 620 of the MRI system 600. The electronics of the power supply system 612 may provide, in some embodiments, operating power to one or more gradient coils (e.g., the gradient coils 628) to generate one or more gradient magnetic fields to provide spatial encoding of the MR signals. Additionally, the electronics of the power supply system 612 may provide operating power to one or more RF coils (e.g., the RF transmit and receive coils 626) to generate and/or receive one or more RF signals from the subject. In some embodiments, the power supply system 612 may include a power supply configured to provide power from mains electricity to the MRI system and/or an energy storage device. The power supply may, in some embodiments, be an AC-to-DC power supply configured to convert AC power from mains electricity into DC power for use by the MRI system. The energy storage device may, in some embodiments, be any one of a battery, a capacitor, an ultracapacitor, a flywheel, or any other suitable energy storage apparatus that may bidirectionally receive (e.g., store) power from mains electricity and supply power to the MRI system. Additionally, the power supply system 612 may include additional power electronics encompassing components including, but not limited to, power converters, switches, buses, drivers, and any other suitable electronics for supplying the MRI system with power.

The amplifiers(s) 614 may include one or more RF receive (Rx) pre-amplifiers that amplify MR signals detected by one or more RF receive coils (e.g., coils 626 shown in FIG. 6), one or more RF transmit (Tx) power components configured to provide power to one or more RF transmit coils (e.g., coils 626 shown in FIG. 6), one or more gradient power components configured to provide power to one or more gradient coils (e.g., gradient coils 628 shown in FIG. 6), and one or more shim power components configured to provide power to one or more shims (e.g., shims 624 shown in FIG. 6). In some embodiments the shim may be implemented using permanent magnets, electromagnetics (e.g., a coil), and/or a combination thereof. Transmit/receive circuitry 616 may be used to select whether RF transmit coils or RF receive coils are being operated.

As illustrated in FIG. 6, the MRI system 600 includes a controller 606 (also referred to as a console) having control electronics to send instructions to and receive information from the power management system 610. The controller 606 may be configured to implement one or more pulse sequences, which are used to determine the instructions sent to the power management system 610 to operate the magnetic components 620 in a desired sequence (e.g., parameters for operating the RF transmit and receive coils 626, parameters for operating the gradient coils 628, etc.).

A pulse sequence generally describes the order and timing in which transmit/receive coils and gradient coils operate to prepare the magnetization of a subject and acquire resulting MR data. In some embodiments, a pulse sequence may indicate an order and duration of transmit pulses, gradient pulses, and acquisition times during which the receive coils acquire MR data.

A pulse sequence may be organized into a series of periods. In some embodiments, a pulse sequence may comprise a pre-programmed number of pulse repetition periods, and applying a pulse sequence may comprise operating the MRI system in accordance with parameters of the pulse sequence for the pre-programmed number of pulse repetition periods. In each period, the pulse sequence may include parameters for generating RF pulses (e.g., parameters identifying transmit duration, waveform, amplitude, phase, etc.), parameters for generating gradient fields (e.g., parameters identifying transmit duration, waveform, amplitude, phase, etc.), timing parameters governing when RF and/or gradient pulses are generated and/or when the receive coil(s) are configured to detect MR signals generated by the subject, etc. In some embodiments, a pulse sequence may include parameters specifying one or more navigator RF pulses.

Embodiments of pulse sequences include zero echo time (ZTE) pulse sequences, balance steady-state free precession (bSSFP) pulse sequences, gradient echo pulse sequences, inversion recovery pulse sequences, diffusion weighted imaging (DWI) pulse sequences, spin echo pulse sequences including conventional spin echo (CSE) pulse sequences, fast spin echo (FSE) pulse sequences, turbo spin echo (TSE) pulse sequences and/or any multi-spin echo pulse sequences such a diffusion weighted spin echo pulse sequences, inversion recovery spin echo pulse sequences, arterial spin labeling pulse sequences, Overhauser imaging pulse sequences, etc.

As illustrated in FIG. 6, the controller 606 also interacts with a computing device 604 programmed to process received MR data. In some embodiments, the computing device 604 may process received MR data to generate one or more MR images using any suitable image reconstruction process(es). The controller 606 may provide information about one or more pulse sequences to the computing device 604 for the processing of data by the computing device. In some embodiments, the controller 606 may provide information about one or more pulse sequences to the computing device 604 and the computing device may perform an image reconstruction process based, at least in part, on the provided information.

The computing device 604 may be any electronic device configured to process acquired MR data and generate one or more images of a subject being imaged. In some embodiments, the computing device 604 may be located in a same room as the MRI system 600 and/or coupled to the MRI system 600. In some embodiments, the computing device 604 may be a fixed electronic device such as a desktop computer, a server, a rack-mounted computer, or any other suitable fixed electronic device that may be configured to process MR data and generate one or more images of the subject being imaged. Alternatively, the computing device 604 may be a portable device such as a smart phone, a personal digital assistant, a laptop computer, a tablet computer, or any other portable device that may be configured to process MR data and generate one or images of the subject being imaged. In some embodiments, the computing device 604 may comprise multiple computing devices of any suitable type, as aspects of the disclosure provided herein are not limited in this respect.

The system 600 may further comprise one or more external sensors 662. In some embodiments, the one or more external sensors may assist in detecting one or more error sources (e.g., motion, noise) which degrade image quality. Information obtained by the one or more external sensors 662 may be used to determine whether to extend imaging, in some embodiments. In some embodiments, information obtained by the one of more external sensors 662 may be used to detect subject presence and/or position, as described herein. The controller 606 may be configured to receive information from the one or more external sensors, in some embodiments. In some embodiments, the controller 606 of the system 600 may be configured to control operations of the one or more external sensors 662.

Figure 7:
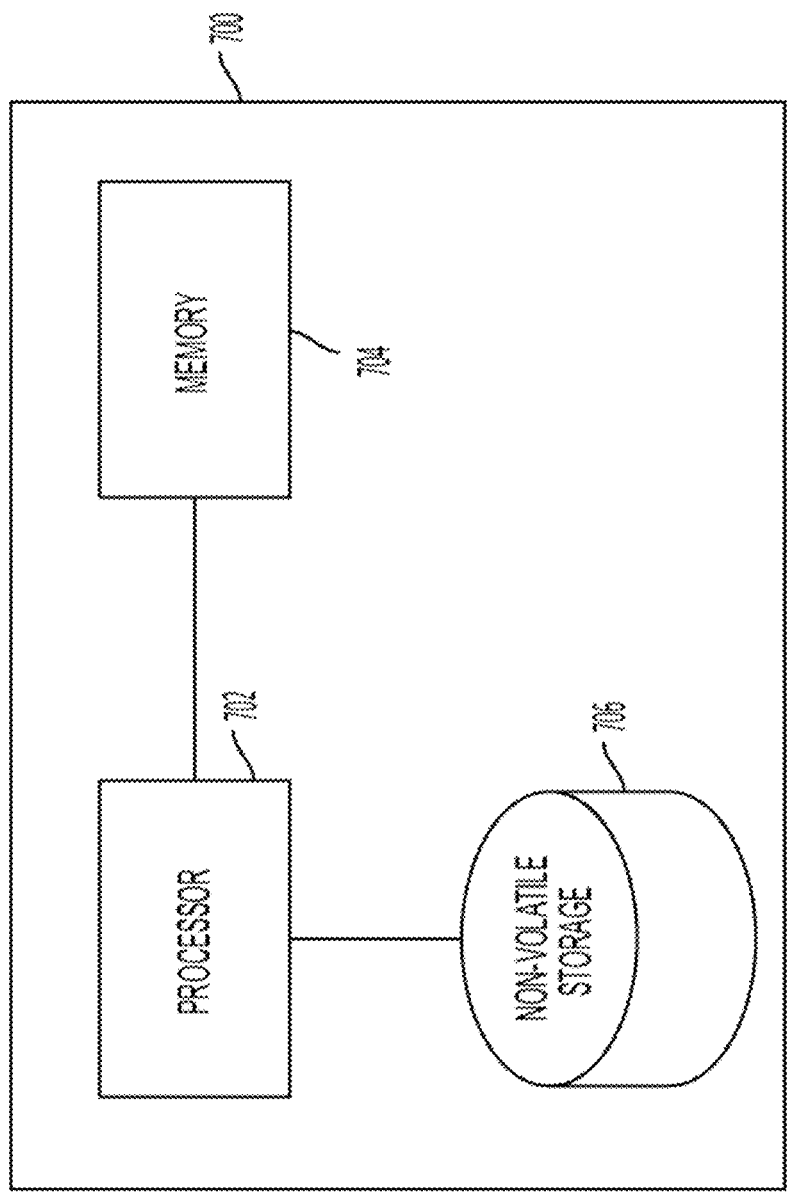
FIG. 7 illustrates a block diagram of an embodiment of a computer system, in accordance with some embodiments of the technology described herein.

FIG. 7 shows a block diagram of an embodiment of a computer system 700 that may be used to implement embodiments of the technology described herein. The computing device 700 may include one or more computer hardware processors 702 and non-transitory computer-readable storage media (e.g., memory 704 shown in FIG. 7 and one or more non-volatile storage devices 706). The processor(s) 702 may control writing data to and reading data from (1) the memory 704; and (2) the non-volatile storage device(s) 706. To perform any of the functionality described herein, the processor(s) 702 may execute one or more processor-executable instructions stored in one or more non-transitory computer-readable storage media (e.g., the memory 704), which may serve as non-transitory computer-readable storage media storing processor-executable instructions for execution by the processor(s) 702.

Figure 8:
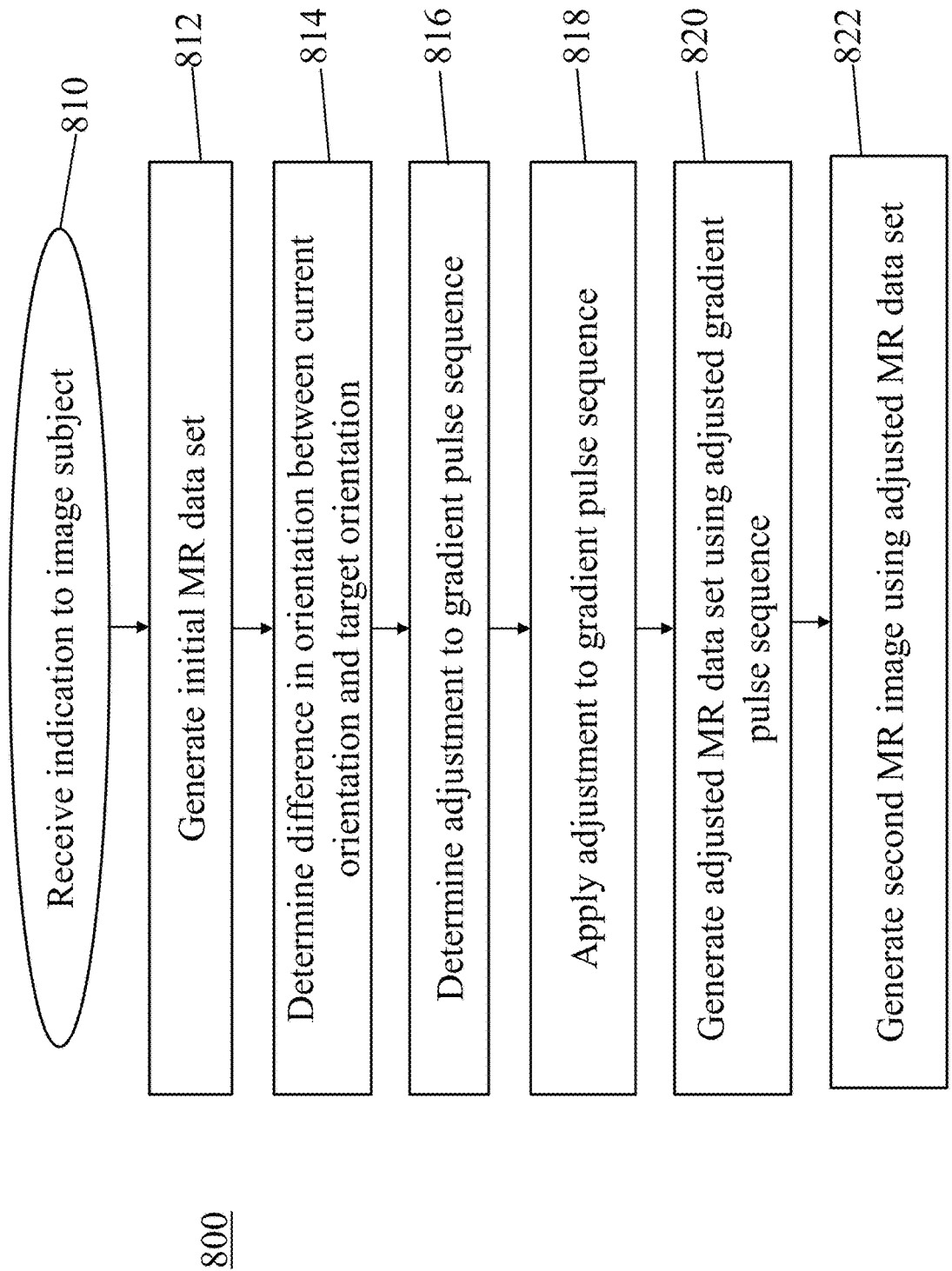
FIG. 8 illustrates an embodiment of a method for imaging a subject using a magnetic resonance imaging device in response to receiving an indication, in accordance with some embodiments of the technology described herein.

An example embodiment of a method for performing magnetic resonance imaging of a subject is provided herein. FIG. 8 illustrates an example method for imaging a subject using a magnetic resonance imaging device in response to receiving an indication, in accordance with some embodiments of the technology described herein.

The method 800 for imaging a subject using a magnetic resonance imaging device in response to receiving an indication may start by receiving an indication to image a subject 810. The indication may comprise any suitable indication as described herein.

Subsequently, in response to receiving the indication, with at least one controller, an initial MR data set may be obtained 812. The initial MR data set may be obtained using at least one RF coil, in accordance with the techniques described herein. The initial MR data may be used to generate an initial MR image.

Subsequently, a difference in orientation between a current orientation of the subject in the initial MR image and a target orientation of the subject may be determined 814. The difference in orientation may be determined in accordance with any of the techniques described herein.

Subsequently, an adjustment to a gradient pulse sequence may be determined 816. The adjustment to the gradient pulse sequence may be determined based on the initial MR image, in accordance with any of the techniques described herein.

Subsequently, the determined adjustment may be applied to the gradient pulse sequence 818 to obtain an adjusted gradient pulse sequence. Applying the adjustment to the gradient pulse sequence may be performed in accordance with any of the techniques described herein.

Subsequently, an adjusted MR data set may be generated using the adjusted gradient pulse sequence 820. The adjusted MR data set may be generated in accordance with any of the techniques described herein.

Subsequently, a second MR image may be generated using the adjusted MR data set 822. The second MR image may be generated in accordance with any of the techniques described herein.

Another example embodiment of a method for performing magnetic resonance imaging with an MRI device with reduced operator interaction is provided herein. The method may be performed by at least one controller of a magnetic resonance imaging system.

In the example embodiment, the method begins with receiving an indication to perform magnetic resonance imaging of a subject (e.g., a human subject, a non-human animal subject, a phantom). In response to receiving the indication from the user, the method autonomously performs the following actions described herein with at least one controller.

First, presence of the subject in the imaging region of the MRI device may be detected. Presence of the subject may be detected according to any of the techniques described herein.

Subsequently, a position and/or orientation of the subject may be assessed. The position of the subject may be assessed according to any of the techniques described herein.

Subsequently, noise levels in the environment of the MRI device may be assessed. Noise levels in the environment of the MRI device may be assessed according to any of the techniques described herein.

Subsequently, a center frequency of the MRI device may be identified. The center frequency may be identified according to any of the techniques described herein.

Subsequently, the main magnetic field generated by the MRI device may be shimmed. Shimming of the main magnetic field may be performed according to any of the techniques described herein.

Subsequently, the radio-frequency power of the MRI device may be calibrated. Calibration of the RF power may be performed according to any of the techniques described herein.

Subsequently, an initial MR image of the subject may be acquired. Acquisition of the initial MR image of the subject may be performed according to any of the techniques described herein.

Subsequently, a type of the subject may be identified (e.g., a particular anatomy of the subject and/or identification of whether the subject is a human subject, a non-human animal subject, or a phantom). Identification of the type of the subject may be performed according to any of the techniques described herein.

Subsequently, a position of the subject may be assessed. The position of the subject may be assessed according to any of the techniques described herein.

Subsequently, a difference in orientation between a current orientation of the subject and a target orientation may be determined. The determination of the difference in orientation between the current orientation of the subject and a target orientation of the subject may be made according to any of the techniques described herein.

Subsequently, a correction to the orientation of the subject may be determined based on the determined difference in orientation between the current orientation and the target orientation. The correction to the orientation of the subject may be determined according to any of the techniques described herein.

Subsequently, the determined orientation correction may be applied. Application of the orientation correction may be performed according to any of the techniques described herein.

Subsequently, it may be determined whether a worklist entry is present for the subject. The determination may be made according to any of the techniques described herein.

Subsequently, recommended protocols for imaging the subject may be determined, including based on the worklist entry for the subject, if present. Determining the recommended protocols for imaging the subject may be performed according to any of the techniques described herein.

Subsequently, the subject may be imaged using the MRI device. In particular, MR data may be collected according to a selected one of the recommended protocols. Collection of the MR data according to the selected protocol may be performed according to any of the techniques described herein.

Subsequently, the collected MR data may be analyzed for pathology and/or artifacts in the MR data to determine whether to adjust subsequent scanning. Analysis of the collected MR data may be performed according to any of the techniques described herein.

Subsequently, subsequent scanning of the subject may be adjusted based on the analysis. Adjustment of subsequent scanning may be performed according to any of the techniques described herein.

In the example embodiment, the method may be performed autonomously in response to an indication to perform MR imaging of a subject. Accordingly, the method may be performed without requiring any further interaction and/or input from a user.

Some embodiments include a system comprising the MRI device and the controller configured to perform the method of the example embodiments. Some embodiments include at least one non-transitory computer-readable storage medium having instructions encoded thereon, that, when executed by at least one controller, cause the at least one controller to perform the method of the example embodiment.

It should be appreciated that certain acts of the techniques described herein are optional, and the techniques described herein may be performed without performing such acts. In some embodiments, one or more of the subject loading and positioning, the automated alignment and image orientation, and the protocol selection may be omitted from method 200. In some embodiments, one or more of detecting a presence of a subject in the MRI device, initial checking of the position of the subject, checking noise levels, finding a center frequency, shimming the main magnetic field, calibrating RF power, acquiring an initial MR image, identifying a subject type, and subsequently checking subject position may be omitted from method 300. In some embodiments, one or more of obtaining an initial MR image, determining a difference in orientation between current orientation and target orientation, determining an orientation correction, applying an orientation correction, and imaging the subject with the corrected orientation may be omitted from method 400. In some embodiments, one or more of determining if a worklist entry is present for the subject, determining recommended protocols for the subject, collecting MR data according to the selected protocol, analyzing MR data for pathology and/or artifacts, and adjusting subsequent scanning based on analysis may be omitted from process 500. In addition, one or more of the acts of the techniques described herein may be repeated any suitable number of times before proceeding to one or more subsequent acts and/or an end of the method.

Systems and methods are provided herein for performing magnetic resonance imaging with reduced operator interaction. As described herein, a method for imaging a subject with a magnetic resonance imaging device may be performed in response to receiving an indication. The method may be performed in response to receiving the indication with the at least one controller. In some embodiments, the method may be performed in response to receiving the indication and without requiring further indications, including any input or interaction from a user. In some embodiments, the method may be performed autonomously with the at least one controller in response to receiving the indication. In some embodiments, each act of the techniques described herein may be performed in response to completion of a prior step, without requiring an indication to proceed.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. Those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The embodiments described herein can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described herein. The computer readable medium or media can be transportable, such that the program or programs stored thereon can be loaded onto one or more different computers or other processors to implement various ones of the aspects described herein. In some embodiments, computer readable media may be tangible (e.g., non-transitory) computer readable media. In some embodiments, the computer readable media may comprise a persistent memory.

The terms "program" or "software" are used herein in a generic sense to refer to any type of computer code or set of computer-executable instructions that can be employed to program a computer or other processor to implement various aspects as described herein. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

The embodiments described herein of the present technology can be implemented in any of numerous ways. The embodiments may be implemented using hardware, software or a combination thereof. When implemented in software, the software code can be executed on any suitable processor or collection of processors, whether provided in a single computer or distributed among multiple computers. It should be appreciated. that any component or collection of components that perform the functions described herein can be generically considered as a controller that controls the functions described herein. A controller can be implemented in numerous ways, such as with dedicated hardware, or with general purpose hardware (e.g., one or more processor) that is programmed using microcode or software to perform the functions described herein, and may be implemented in a combination of ways when the controller corresponds to multiple components of a system.

Further, it should be appreciated that a computer may be embodied in any of a number of forms, such as a rack-mounted computer, a desktop computer, a laptop computer, or a tablet computer, as non-limiting embodiments. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Embodiments of output devices that can be used to provide a user interface include printers or display screens for visual presentation of output and speakers or other sound generating devices for audible presentation of output. Embodiments of input devices that can be used for a user interface include keyboards, and pointing devices, such as mice, touch pads, and digitizing tablets. In an embodiment, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification herein, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The terms "substantially", "approximately", and "about" may be used to mean within ±20% of a target value in some embodiments, within ±10% of a target value in some embodiments, within ±5% of a target value in some embodiments, within ±2% of a target value in some embodiments. The terms "approximately" and "about" may include the target value.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method for imaging a subject using a magnetic resonance (MR) imaging (MRI) system including at least one gradient coil, at least one radio-frequency (RF) coil, and at least one controller, the method comprising:
   receiving an indication to image the subject using the MRI system; and
   in response to receiving the indication, with the at least one controller:
      generating, using the at least one RF coil, an initial MR data set for generating an initial image of the subject;
      determining, using the initial MR image of the subject, a difference in orientation between a current orientation of the subject in the initial MR image and a target orientation of the subject;
      determining, using the determined difference in orientation, an adjustment to a gradient pulse sequence for controlling the at least one gradient coil;
      applying the determined adjustment to the gradient pulse sequence to obtain an adjusted gradient pulse sequence;
      generating an adjusted MR data set using the adjusted gradient pulse sequence; and
      generating a second MR image of the subject using the adjusted MR data set.

2. A magnetic resonance (MR) imaging (MRI) system for imaging a subject, the MRI system comprising:
   at least one gradient coil;
   at least one radio-frequency (RF) coil; and
   at least one controller configured to:
      receive, an indication to image the subject using the MRI system; and
      in response to receiving the indication, with the at least one controller:
         generate, using the at least one RF coil, an initial MR data set for generating an initial image of the subject;
         determine, using the initial MR image of the subject, a difference in orientation between a current orientation of the subject in the initial MR image and a target orientation of the subject;
         determine, using the determined difference in orientation, an adjustment to a gradient pulse sequence for controlling the at least one gradient coil;
         apply the determined adjustment to the gradient pulse sequence to obtain an adjusted gradient pulse sequence;
         generate an adjusted MR data set using the adjusted gradient pulse sequence; and
         generate a second MR image of the subject using the adjusted MR data set.

3. At least one non-transitory computer-readable storage medium having encoded thereon executable instructions that, when executed by at least one computer hardware processor, cause the at least one computer hardware processor to perform a method for imaging a subject using a magnetic resonance (MR) imaging (MRI) system, the MRI system comprising at least one gradient coil, at least one radio-frequency (RF) coil, and at least one controller, the method comprising:
   receiving an indication to image the subject using the MRI system;
   in response to receiving the indication, with the at least one controller;
      generating, using the at least one RF coil, an initial MR data set for generating an initial image of the subject;
      determining, using the initial MR image of the subject, a difference in orientation between a current orientation of the subject in the initial MR image and a target orientation of the subject;
      determining, using the determined difference in orientation, an adjustment to a gradient pulse sequence for controlling the at least one gradient coil;
      applying the determined adjustment to the gradient pulse sequence to obtain an adjusted gradient pulse sequence;
      generating an adjusted MR data set using the adjusted gradient pulse sequence; and
      generating a second MR image of the subject using the adjusted MR data set.

4. The method of claim 1, wherein determining the difference in orientation between the current orientation of the subject and the target orientation of the subject comprises comparing the initial MR image of the subject to a template MR image having the target orientation.

5. The method of claim 4, wherein determining the difference in orientation comprises determining the difference in orientation between the current orientation of the subject in the initial MR image and the target orientation of the subject in the template MR image about each of three substantially perpendicular axes.

6. The method of claim 4, wherein determining the difference in orientation between the current orientation of the subject and the target orientation of the subject comprises determining a difference in orientation between a portion of the initial MR image and a portion of the template MR image.

7. The method of claim 1, further comprising, based on the initial MR image of the subject and/or information about the at least one RF coil, determining a type of the subject.

8. The method of claim 7, wherein determining the type of the subject comprises identifying an anatomy that the subject comprises.

9. The method of claim 7, wherein determining the type of the subject comprises identifying the subject as one of a human subject, a non-human animal subject, or a phantom.

10. The method of claim 1, further comprising based on the initial MR image and/or an anatomy that the subject comprises, identifying one or more candidate pulse sequences for controlling the at least one RF coil and wherein generating the adjusted MR data set further comprises using the identified one or more candidate pulse sequences.

11. The method of claim 1, wherein determining the difference in orientation further comprises determining the difference in orientation using information about the at least one RF coil.

12. The method of claim 1, further comprising:
determining, using the determined difference in orientation, an adjustment to an RF pulse sequence for controlling the at least one RF coil;
applying the determined adjustment to the RF pulse sequence to obtain an adjusted RF pulse sequence; and
wherein generating the adjusted MR data set further comprises using the adjusted RF pulse sequence.

13. The method of claim 1, further comprising:
determining, using the determined difference in orientation, an adjustment to image reconstruction parameters to compensate for the adjusted gradient pulse sequence and the adjusted RF pulse sequence; and
wherein generating the second MR image of the subject further comprises using the determined adjustment to the image reconstruction parameters.

14. The method of claim 1, wherein the acquiring the initial MR data set, determining the difference in orientation, determining the adjustment to the gradient pulse sequence, generating the adjusted MR data set and generating the second MR with the at least one controller is performed autonomously in response to receiving the indication.

15. The MRI system of claim 2, wherein the at least one controller is configured to determine the difference in orientation between the current orientation of the subject and the target orientation of the subject at least in part by comparing the initial MR image of the subject to a template MR image having the target orientation.

16. The MRI system of claim 15, wherein the at least one controller is configured to determine the difference in orientation at least in part by determining the difference in orientation between the current orientation of the subject in the initial MR image and the target orientation of the subject in the template MR image about each of three substantially perpendicular axes.

17. The MRI system of claim 2, wherein the at least one controller is further configured to, in response to receiving the indication, based on the initial MR image of the subject and/or information about the at least one RF coil, determine a type of the subject.

18. The MRI system of claim 2, wherein the at least one controller is further configured to, in response to receiving the indication, based on the initial MR image and/or an anatomy that the subject comprises, identify one or more candidate pulse sequences for controlling the at least one RF coil and wherein the at least one controller is configured to generate the adjusted MR data set at least in part by using the identified one or more candidate pulse sequences.

19. The MRI system of claim 2, wherein a strength of a $B_0$ magnetic field generated by the MRI system is greater than or equal to 50 mT and less than or equal to 0.1 T.

* * * * *